US008557737B2

(12) United States Patent
Cotterill

(10) Patent No.: US 8,557,737 B2
(45) Date of Patent: Oct. 15, 2013

(54) METHODS OF ALTERING POPPY CHARACTERISTICS

(75) Inventor: Paul Cotterill, Latrobe (AU)

(73) Assignee: GlaxoSmithKline Australia, Pty, Ltd, Boronia, Victoria (AU)

( * ) Notice: Subject to any disclaimer, the term of this patent is extended or adjusted under 35 U.S.C. 154(b) by 1253 days.

(21) Appl. No.: 12/064,429

(22) PCT Filed: Aug. 17, 2006

(86) PCT No.: PCT/AU2006/001181
§ 371 (c)(1),
(2), (4) Date: Jul. 7, 2008

(87) PCT Pub. No.: WO2007/022561
PCT Pub. Date: Mar. 1, 2007

(65) Prior Publication Data
US 2008/0269058 A1 Oct. 30, 2008

(30) Foreign Application Priority Data
Aug. 23, 2005 (AU) .............................. 2005904577

(51) Int. Cl.
*A01N 47/36* (2006.01)
(52) U.S. Cl.
USPC .......................................................... 504/212
(58) Field of Classification Search
USPC .......................................................... 504/212
See application file for complete search history.

(56) References Cited

FOREIGN PATENT DOCUMENTS

| AU | 9183693 | 3/1992 |
| EP | 1053679 | 11/2000 |
| EP | 1916889 B1 | 3/2010 |
| WO | WO9802033 | 1/1998 |
| WO | WO9935902 | 7/1999 |

OTHER PUBLICATIONS

Bresnahan et al., Glyphosate applied preharvest induces shikimic acid accumulation in hard red spring wheat (*Triticum aestivum*), J Agric Food Chem 51: 4004 (2003).*
Field Pea: Western NSW Planting Guide, Feb. 2005.*
Wittwer et al., Plant Physiol. 25: 539 (1950).*
Baldwin, Chemical weed control in oil-seed poppy (*Papaver somniferum*), Aust J Exp Agric Animal Husbandry 17: 837 (1977).*
Bulletin of the Lloyd Library of Botany, Pharmacy and Materia Medica 18: 85-76 (1911) (ed. J.U.& C.G. Lloyd).*
Cirujeda et al., "A qualitative quick-test for detection of herbicide resistance to tribenuron-mehtyl in *Papaver rhoeas*" Weed Research (Dec. 2001) 41(6):523-534.
Duran-Prado et al., "Molecular basis of resistance to sulfonylureas in *Papaver rhoeas*" Pesticide Biochemistry & Physiology (May 2004) 79(1):10-17.

Blair et al., "A Review of the Activity, Fate and Mode of Action of Sulfonylurea Herbicides" Pesticide Science (Jan. 1988) 22(3):195-219.
Obrigawitch et al., "Assessment of effects on non-target plants from sulfonylurea herbicides using field approaches" Pesticide Science (Mar. 1998) 52(3):199-217.
Scarabel et al., "Molecular basis and genetic characterization of evolved resistance to ALS-inhibitors in *Papaver rhocas*" Plant Science (Mar. 2004) 166(3):703-709.
Fachini et al., "Uncoupled Defense Gene Expression and Antimicrobial Alkaloid Accumulation in Elicited Opium Poppy Cell Cultures" Plant Physiology (Jan. 1996) 111:687-697.
Chauhan, S.P. et al. Mutagenic Effects of Combined and Single Doses of Gamma Rays and EMS in Opium Poppy. Plant Breeding (1993) 110(4):342-345.
Floria, F. et al. The Influence of Some Successive Mutagenic Treatments on the Capsules Dimensions and the Morphine Content of *Papaver somniferum* L. Revue Roumaine de Biochemie (1986) 23(4):285-292.
Ghiorghita, G.I. et al. "The Morphine Content—A Selection Criterion in Obtaining Some More Productive Forms of *Papaver somniferum* by Means of Experimental Mugogenesis I: Effects of the Successful Treatment with Gamma Rays and Alkylating Agents in the 4$^{th}$ Generation" Revue Roumaine de Biochemie (1984) 21(4):279-286.
Gaurab Bhardwaj; From Pioneering Invention to Sustained Innovation: The Story of Sulfonylurea Herbicides; Submitted for Review to Chemical Heritage, May 26, 2005.
Boutin et al.; Effects of the Sulfonylurea Herbicide Metsulfuron Methyl on Growth and Reproduction of Five Wetland and Terrestrial Plant Species; Environmental Toxicology and Chemistry, vol. 19, No. 10, pp. 2532-2541, 2000.
Robert J. Bryant; Fifth SCI Process Development Symposium; Paper presented at a meeting of the Fine Chemicals Group of the SCI, held in Birmingham on Nov. 11, 1987.
Forbes et al.; The potential for use of growth regulators in poppy production; Crop and pasture production—science and practice. Edited by J.J Yates. Proceedings of the 3rd Australian Agronomy Conference, Jan.-Feb. 1985, The University of Tasmaina, Hobart, Tasmania.
Gealy et al.; Growth and Yield of Pea (*Pisum sativum* L.) and Lentil (*Lens culinaris* L.) Sprayed with Low Rates of Sulfonylurea and Phenoxy Herbicides; Weed Science, vol. 43, pp. 640-647, 1995.
Lyon et al.; Mon 37500 Soil Residues Affect Rotational Crops in the High Plains; Weed Technology, vol. 17, pp. 792-798, 2003.
Mitchem et al.; Evaluation of Chlorimuron as a Growth Regulator for Peanut; Peanut Science; vol. 22, pp. 62-66, 1995.
Patterson et al.; Effects of Chlorimuron Applied Post emergence to Cotton (*Gossypium hirsutum*); Weed Technology, vol. 4, pp. 314-317, 1990.
Bruce Mounster: Short Poppy Shock Bonus; Tasmanian Country, Friday May 7, 2004.
Compendium of Pesticide Common Names; http: /www.alalwood.net/pesticides/index.html, 2011.
Data Sheet from the Compendium of Pesticide Common Names; http://www.alanwood.net/pesticides/clopyralid.html, Downloaded Jul. 28, 2011.

* cited by examiner

Primary Examiner — James H Alstrum Acevedo
Assistant Examiner — Thor Nielsen
(74) Attorney, Agent, or Firm — Nora L. Stein; Theodore R. Furman

(57) ABSTRACT

The present invention relates to the use of sulfonylurea compounds to alter physical and/or growth characteristics of poppy plants.

18 Claims, No Drawings

METHODS OF ALTERING POPPY CHARACTERISTICS

This application is a 371 national phase entry of International Application No. PCT/AU2006/001181, filed 17 Aug. 2006.

FIELD OF THE INVENTION

The present invention relates generally to the application of sulfonylurea compounds to poppy plants and/or their loci in order to alter physical and/or growth characteristics of the plants. Advantageously, one or more of these altered characteristics may lead to improvements or advantages in harvesting of the plants or, desirably, to an increase in the alkaloid yield of the poppy plant and/or recovery of alkaloid from the plant.

BACKGROUND OF THE INVENTION

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

The milky liquid or latex derived from the unripe capsules of *Papaver somniferum* (or the opium poppy) has for many centuries been known to possess medicinal and mind altering properties. For example, ancient civilisations such as the ancient Egyptians used poppy latex in treatment for sleep inducement. The dried and powered form of latex is called opium. Opium comprises about five distinct chemical classes: phenanthrene, benzylisoquinoline, tetrahydroisoquinidine, cryptopine and miscellaneous. The alkaloid phenanthrenes, morphine, codeine and thebaine are therapeutic drugs. While thebaine is not medicinally useful in itself, it is usually converted into a useful derivative. Morphine and codeine are used principally for sedation and as analgesics. Given the low yields associated with synthetic approaches to these alkaloids, extraction from opium or poppy straw remains the major source of these compounds.

Several factors can adversely affect the alkaloid yield of and/or recovery from a given capsule obtained from poppy plant. Plant lodging, wherein the stem is displaced from its normal, essentially upright position, can result in poppy capsules lying close to or on the ground. As a consequence, the capsules may become weakened and alkaloid can leach out. Furthermore, significant lodging necessitates a different harvesting process which in itself may result in a decrease in the alkaloid recoverable from the capsule. Plant height can also affect alkaloid recovery. The straw obtained by harvesting poppy capsules contains a portion of stem as well as the capsule. Since the majority of the alkaloid is formed in the capsule, a large proportion of stem in the final straw reduces the amount of alkaloid recoverable from the straw. Similarly, if the ratio of seed weight to capsule weight is great, this could also decrease alkaloid yield or recovery.

Sulfonylurea compounds represent one of the largest classes of herbicides. These herbicides inhibit cell division and growth by inhibiting acetolactate synthase, a key enzyme in the first step of the biosynthesis of branched chain amino acids in bacteria, fingi and certain plants. Sulfonylureas are absorbed by plant foliage and roots to be transported to the tissues of the plant where cell division occurs. Cellular processes such as protein synthesis, nucleic acid synthesis, respiration and photosynthesis are not directly inhibited by these compounds, and thus the sulfonlyureas also provide excellent crop safety and low acute toxicity to humans and animals. Application rates of sulfonylureas for herbicidal purposes are typically in the g/ha level (compared to the kg/ha level for other typical herbicides), depending on the crop of interest. Typical ranges of use rates for a number of sulfonylurea herbicides, as applied to certain crops, are provided below (Russell, M. H. et al, *Pesticide Outlook*—August 2002, 166-173):

| | | |
|---|---|---|
| azimsulfuron | (rice) | 5-25 g/ha |
| bensulfuron methyl | (rice) | 20-70 g/ha |
| chlorimuron ethyl | (soybean, peanuts) | 8-13 g/ha |
| chlorsulfuron | (cereals, vegetable) | 9-25, 17-157 g/ha |
| ethametsulfuron methyl | (oilseed rape) | 15-23 g/ha |
| flupyrsulfuron methyl | (cereals) | 8-10 g/ha |
| iodosulfuron methyl sodium | (wheat) | 7.5-10 g/ha |
| mesosulfuron methyl | (wheat) | 10 g/ha |
| metsulfuron methyl | (cereals, rice, vegetable) | 3-7.5, 14-168 g/ha |
| nicosulfuron | (maize) | 35-70 g/ha |
| rimsulfuron | (maize, potatoes, tomatoes) | 5-35 g/ha |
| sulfometuron | (vegetable) | 26-420 g/ha |
| sulfometuron methyl | (commercial/industrial areas, rights of way) | 150-600 g/ha |
| sulfosulfuron | (cereals) | 15-20 g/ha |
| thifensulfuron methyl | (cereals, maize, soybeans) | 2-30 g/ha |
| tribenuron methyl | (cereals) | 9-18 g/ha |
| triasulfuron | (sugar beet) | 18-35 g/ha |
| trifloxysulfuron sodium | (cotton) | 11-23 g/ha |

It has now unexpectedly been found that the application of certain sulfonylurea compounds to poppy plants, in amounts substantially less than those used for herbicidal activity, can alter one or more characteristics of the poppy plants, including reduction in plant height, reduction in lodging, reduction in seed weight and an increase in straw weight (through an increased weight proportion of capsule). One or more of these effects may advantageously provide improvements in harvesting of the poppy plants or, preferably, an increase in the alkaloid yield and/or recovery from the poppy plant.

SUMMARY OF THE INVENTION

The present invention relates to methods for altering the characteristics of poppy plants, specifically to effecting one or more of reduction in the height of a poppy plant, reduction in the lodging of a poppy plant, reduction in seed weight of a poppy plant, increase in capsule weight of a poppy plant, increase in straw weight and increase in alkaloid yield and/or recovery.

Thus, in a first aspect, the invention provides a method for effecting one or more of: reduction in the height of a poppy plant, reduction in the lodging of a poppy plant, reduction in the seed weight of a poppy plant and increase in capsule weight of a poppy plant, comprising the step of applying an effective amount of a sulfonylurea compound or agriculturally acceptable salt or ester thereof to said poppy plant or locus thereof.

In one embodiment, the present invention provides a method of reducing the height of a poppy plant comprising the step of applying a height reducing effective amount of a sulfonylurea compound or agriculturally acceptable salt or ester thereof to said poppy plant or locus thereof.

Another embodiment of the invention provides a method of reducing lodging of a poppy plant comprising the step of applying a lodging reducing effective amount of a sulfonylurea compound or agriculturally acceptable salt or ester thereof to said poppy plant or locus thereof.

Still yet another embodiment of the invention provides a method of reducing the seed weight of a poppy plant comprising the step of applying a seed weight reducing effective amount of a sulfonylurea compound or agriculturally acceptable salt or ester thereof to said poppy plant or locus thereof.

Still yet another embodiment of the invention provides a method of increasing the capsule weight of a poppy plant comprising the step of applying a capsule weight increasing effective amount of a sulfonylurea compound or agriculturally acceptable salt or ester thereof to said poppy plant or locus thereof.

Through one or more of a reduction in stem height, reduction in seed weight and increase in capsule weight, the straw weight obtained from the poppy plants may be improved.

Accordingly, another aspect of the invention provides a method of increasing straw weight obtained from a poppy plant comprising the step of applying a straw weight increasing effective amount of a sulfonylurea compound or agriculturally acceptable salt or ester thereof to said poppy plant or locus thereof.

The result of one or more of the above-mentioned methods may advantageously afford an increase in the alkaloid yield of the poppy plant and/or recovery of the alkaloid from the plant.

Accordingly, a further aspect of the present invention provides a method of increasing alkaloid yield and/or recovery from a poppy plant comprising the step of applying an alkaloid yield and/or recovery increasing effective amount of a sulfonylurea compound or agriculturally acceptable salt or ester thereof to said poppy plant or locus thereof.

Yet another aspect of the invention provides a method of obtaining alkaloid from a poppy plant comprising the steps of:
 (i) applying an amount of a sulfonylurea compound or agriculturally acceptable salt or ester thereof which is effective in reducing the height, lodging or seed weight or increasing capsule weight, alkaloid yield or alkaloid recovery, to said poppy plant or locus thereof;
 (ii) harvesting poppy capsules and forming a straw therefrom; and
 (iii) extracting the alkaloid from the straw.

Preferably, the step of extraction in (iii) comprises either solvent or aqueous extraction to form a concentrate of poppy straw.

Still yet another aspect of the invention provides a method of obtaining alkaloid from a poppy plant comprising the steps of:
 (i) applying an amount of a sulfonylurea compound or agriculturally acceptable salt or ester thereof which is effective in reducing the height, lodging or seed weight or increasing capsule weight, alkaloid yield or alkaloid recovery, to said poppy plant or locus thereof;
 (ii) harvesting opium from immature poppy capsules; and
 (iii) extracting the alkaloid from the opium.

The invention also contemplates mature and/or immature poppy capsules obtained from poppy plants to which an above described characteristic altering effective amount of sulfonylurea compound has been applied, as well as the straw, concentrate of poppy straw, opium and alkaloid produced therefrom.

In one preferred embodiment, the sulfonylurea compound or agriculturally acceptable salt or ester thereof is metsulfuron-methyl.

DETAILED DESCRIPTION OF THE INVENTION

The singular forms "a", "an" and "the" include plural aspects unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The present invention utilizes sulfonylurea compounds, such as sulfonylurea herbicides, to reduce stem height of a poppy plant, and/or reduce lodging of poppy plants, and/or reduce the seed weight and/or increase capsule weight. Preferably, one or more of these effects leads to an increase in alkaloid yield and/or recovery from poppy plants.

As used herein, a "sulfonylurea compound" refers to a compound containing the sulfonylurea moiety (a):

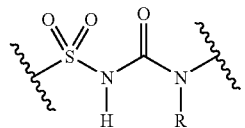

wherein R is H or a $C_{1-4}$alkyl group.

Of particular interest are the class of sulfonylurea compounds which have herbicide activity.

Sulfonylurea compounds useful in the present invention are well known in the art and may be readily synthesized using techniques generally known to synthetic organic chemists including those described in the US patents and applications listed herein. Compounds and compositions thereof may also be purchased commercially.

Exemplary sulfonylurea compounds, and methods for their synthesis, are described and exemplified in U.S. Pat. Nos. 4,013,706; 4,127,405; 4,169,719; 4,370,480; 4,383,113; 4,394,506; 4,420,325; 4,514,212; 4,518,776; 4,546,179; 4,599,412; 4,746,353; 4,789,393; 4,931,580; 5,298,480; 5,461,026; 5,559,079; 5,859,348; 6,096,682; 6,455,470; 6,762,305, 6,806,229, and US Patent Application 2004/0023803; the contents of which are incorporated herein by reference in their entireties for all purposes.

The sulfonyl and amido terminii of the sulfonylurea moiety (a), above, are attached to further groups (referred to herein as A and B respectively). Sulfonylurea compounds contemplated herein include compounds where A and B independently are: optionally substituted aryl, optionally substituted heteroaryl, optionally substituted benzyl, optionally substituted aryloxy (such as optionally substituted phenoxy), optionally substituted arylamino (such as optionally substituted phenyl amino) and (alkylsulfonyl)(N-alkyl)amino. One group of such compounds is where A is any of the above mentioned groups and B is an optionally substituted aryl, or optionally substituted heteroaryl group.

In one embodiment of the invention, the sulfonylurea compounds contemplated herein include those of Formula (I):

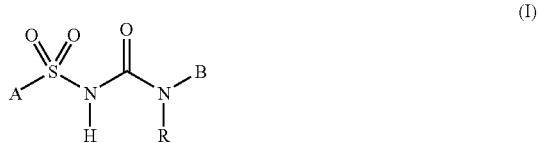

wherein A and B are independently an optionally substituted aryl or optionally substituted heteroaryl group, and R is H or $C_{1-4}$ alkyl. Preferably any heteroaryl A or B group is attached to the sulfonylurea moiety via a carbon atom ring member. R is preferably H or Me.

In a more preferred embodiment, the sulfonylurea compound is a compound of formula (Ia)

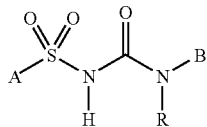

(Ia)

wherein A is an optionally substituted phenyl group or 5-6-membered or 9-10-membered heteroaryl group; and B is an optionally substituted 5-6-membered heteroaryl group.

In one preferred subgroup of formula (Ia), A is an optionally substituted phenyl group or optionally substituted 5-6- or 9-10-membered heteroaryl group, said phenyl or heteroaryl group selected from:

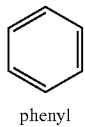
phenyl
(i)

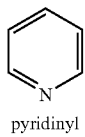
pyridinyl
(ii)

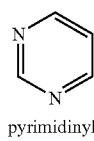
pyrimidinyl
(iii)

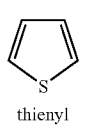
thienyl
(iv)

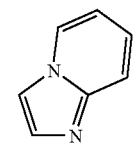
imidazo-pyridinyl
(v)

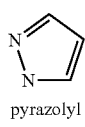
pyrazolyl
(vi)

In another preferred subgroup of formula (Ia), B is an optionally substituted 6-membered heteroaryl group, said heteroaryl group selected from:

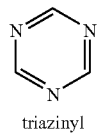
triazinyl
(i)

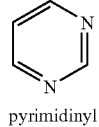
pyrimidinyl
(ii)

A particularly preferred subgroup of formula (Ia) is where A is an optionally substituted 6-membered aryl or 5-6- or 9-10-membered heteroaryl group, said group selected from:

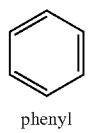
phenyl
(i)

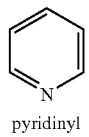
pyridinyl
(ii)

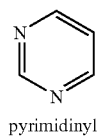
pyrimidinyl
(iii)

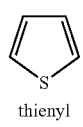
thienyl
(iv)

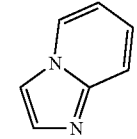
imidazo-pyridinyl
(v)

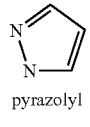
pyrazolyl
(vi)

and wherein B is an optionally substituted 6-membered heteroaryl group, said heteroaryl group selected from:

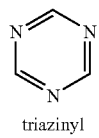
triazinyl
(i)

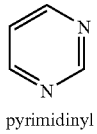
pyrimidinyl

As used herein, the term "aryl" or "ar" (as used in compound terms) denotes any of single, polynuclear, conjugated and fused residues of aromatic hydrocarbon ring systems.

Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Preferred aryl include 6-membered aryl (phenyl) and 10-membered aryl (naphthyl).

The term "heteroaryl" includes any of monocyclic, polycyclic, fused or conjugated hydrocarbon residues, wherein one or more carbon atoms are replaced by a heteroatom so as to provide an aromatic residue. Preferred heteroaryl have 3-20 ring atoms, eg 3-10. Particularly preferred heteroaryl are 5-6 and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl (pyridinyl), pyrrolyl, thienyl, imidazolyl, imadazopyridinyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, isothiazolyl, isoxazolyl, triazolyl, tetrazolyl, oxadialzolyl, oxatriazolyl, triazinyl, and furazanyl.

In this specification "optionally substituted" is taken to mean that a group may or may not be further substituted or fused (so as to form a condensed polycyclic group) with one, two, three or more of organic and inorganic groups, including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloalkoxy, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyalkoxy, hydroxyaralkyl, alkoxy, alkoxyalkyl, alkoxyalkoxy, alkoxyalkenyl, alkoxyalkynyl, alkoxycarbocyclyl, alkoxyaryl, alkoxyheterocyclyl, alkoxyheteroaryl, alkoxyacyl, alkoxyacyloxy, alkoxyaralkyl, alkoxyacyloxyalkyl, (alkoxyacyloxy)haloalkyl, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino (NH$_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulfonyl, alkylsulfonyloxy, alkylsulfonylamino, (alkylsulfonylamino) alkyl, arylsulfenyloxy, alkylsulfenyl, arylsulfenyl, thio, alkylthio, alkenylthio, alkynylthio, arylthio, aralkylthio, carbocyclylthio, heterocyclylthio, heteroarylthio, acylthio, cyano, sulfate and phosphate groups. Optional substitution may also be taken to refer to where a CH$_2$ group in a chain or ring is replaced by a carbonyl group (C=O), or where 2 adjacent carbon atoms are substituted by one end each of a divalent heteroatom containing group so as to form a heterocyclyl group.

Some preferred optional substitutents include alkyl, (eg C$_{1-6}$alkyl such as methyl, ethyl, propyl, butyl, cyclopropyl, cyclobutyl, cyclopentyl or cyclohexyl), hydroxyalkyl (eg hydroxymethyl, hydroxyethyl, hydroxypropyl), hydroxyalkoxy, alkoxyalkyl (eg methoxymethyl, methoxyethyl, methoxypropyl, ethoxymethyl, ethoxyethyl, ethoxypropyl etc), alkoxy (eg C$_{1-6}$ alkoxy such as methoxy, ethoxy, propoxy, butoxy, cyclopropoxy, cyclobutoxy), C$_{1-6}$alkoxyC$_{1-6}$ alkoxy (eg methoxymethoxy, methoxyethoxy etc), halo, haloC$_{1-6}$ alkoxy(eg trifluoromethyl, trichloromethyl, tribromomethyl), haloC$_{1-6}$alkoxy (eg OCH$_2$CF$_3$, OCH$_2$CCl$_3$), hydroxy, phenyl (which itself may be further substituted eg, by C$_{1-6}$alkyl, halo, hydroxy, hydroxyC$_{1-6}$alkyl, C$_{1-6}$alkoxy, haloC$_{1-6}$alkyl, cyano, nitro, OC(O)C$_{1-6}$alkyl, and amino), benzyl (wherein benzyl itself may be further substituted eg, by C$_{1-6}$alkyl, halo, hydroxy, hydroxyC$_{1-6}$alkyl, C$_{1-6}$alkoxy, haloC$_{1-6}$alkyl, cyano, nitro OC(O)C$_{1-6}$alkyl, and amino), phenoxy (wherein phenyl itself may be further substituted eg, by C$_{1-6}$alkyl, halo, hydroxy, hydroxyC$_{1-6}$alkyl, C$_{1-6}$alkoxy, haloC$_{1-6}$alkyl, cyano, nitro OC(O)C$_{1-6}$alkyl, and amino), benzyloxy (wherein benzyl itself may be further substituted eg, by C$_{1-6}$alkyl, halo, hydroxy, hydroxyC$_{1-6}$alkyl, C$_{1-6}$alkoxy, haloC$_{1-6}$alkyl, cyano, nitro OC(O)C$_{1-6}$alkyl, and amino), amino, alkylamino (eg C$_{1-6}$alkyl, such as methylamino, ethylamino, propylamino etc), dialkylamino (eg C$_{1-6}$alkyl, such as dimethylamino, diethylamino, dipropylamino), acylamino (eg NHC(O)CH$_3$), phenylamino (wherein phenyl itself may be further substituted eg, by C$_{1-6}$alkyl, halo, hydroxy, hydroxyC$_{1-6}$alkyl, C$_{1-6}$alkoxy, haloC$_{1-6}$alkyl, cyano, nitro, OC(O)C$_{1-6}$alkyl, and amino), nitro, formyl, —C(O)-alkyl (eg C$_{1-6}$ alkyl, such as acetyl), O—C(O)-alkyl (eg C$_{1-6}$alkyl, such as acetyloxy), benzoyl (wherein the phenyl group itself may be further substituted eg, by C$_{1-6}$alkyl, halo, hydroxy, hydroxyC$_{1-6}$alkyl, C$_{1-6}$alkoxy, haloC$_{1-6}$alkyl, cyano, nitro OC(O)C$_{1-6}$alkyl, and amino), CO$_2$H, CO$_2$alkyl (eg C$_{1-6}$ alkyl such as methyl ester, ethyl ester, propyl ester, butyl ester), CO$_2$phenyl (wherein phenyl itself may be further substituted eg, by C$_{1-6}$alkyl, halo, hydroxy, hydroxyC$_{1-6}$alkyl, C$_{1-6}$alkoxy, haloC$_{1-6}$alkyl, cyano, nitro OC(O)C$_{1-6}$alkyl, and amino), CO$_2$benzyl (wherein benzyl itself may be further substituted eg, by C$_{1-6}$alkyl, halo, hydroxy, hydroxyC$_{1-6}$alkyl, C$_{1-6}$alkoxy, haloC$_{1-6}$alkyl, cyano, nitro OC(O)C$_{1-6}$alkyl, and amino), CONH$_2$, CONHphenyl (wherein phenyl itself may be further substituted eg, by C$_{1-6}$alkyl, halo, hydroxy, hydroxyC$_{1-6}$ alkyl, C$_{1-6}$alkoxy, haloC$_{1-6}$alkyl, cyano, nitro, OC(O)C$_{1-6}$ alkyl, and amino), CONHbenzyl (wherein benzyl itself may be further substituted eg, by C$_{1-6}$alkyl, halo, hydroxy, hydroxyC$_{1-6}$alkyl, C$_{1-6}$alkoxy, haloC$_{1-6}$alkyl, cyano, nitro, OC(O)C$_{1-6}$alkyl, and amino), CONHalkyl (eg C$_{1-6}$ alkyl such as methyl ester, ethyl ester, propyl ester, butyl amide) and CONHdialkyl (eg C$_{1-6}$alkyl), C$_{1-6}$alkylsulfonyl (eg SO$_2$Me, SO$_2$Et, SO$_2$Pr), C$_{1-6}$alkylheteroaryl, (alkoxyacetyloxy)haloC$_{1-6}$alkyl, alkylsulfonylaminoalkyl, replacement of CH$_2$ with C=O, and where 2 adjacent carbon atoms are substituted by one end each of a —O—(CH$_2$)$_n$—O— or —NR'—(CH$_2$)$_n$—NR' wherein n is 1 or 2 and each R' is independently H or C$_{1-6}$alkyl.

Particularly preferred optional substituents include: C$_{1-6}$ alkoxy (e.g. OMe, OEt, OPr, OBu), CO$_2$H, halo (e.g. Cl, I), C(O)C$_{1-6}$alkyl (e.g. C(O)Me, C(O)Et, C(O)$_n$Pr, C(O)iPr, C(O)cyclopropyl), haloC$_{1-6}$alkyl (e.g. CH$_2$Cl, CH$_2$F, CHCl$_2$, CHF$_2$, CCl$_3$, CBr$_3$, CF$_3$, CH—$_2$CF$_3$, (CH$_2$)$_2$CF$_3$), C$_{1-6}$alkyl (e.g. Me, Et, Pr, Bu), amido (e.g. C(O)NH$_2$, C(O)NHMe, C(O)NHEt, C(O)NHPr, C(O)NMe$_2$, C(O)NEt$_2$, C(O)NPr$_2$), haloC$_{1-6}$alkoxy (e.g. OCH$_2$Cl, OCH$_2$F, OCHCl$_2$, OCHF$_2$, OCCl$_3$, OCF$_3$, OCBr$_3$, O(CH$_2$)$_2$Cl, O(CH$_2$)$_2$F, O(CH$_2$)$_3$Cl, O(CH$_2$)$_2$F, OCH$_2$CF$_3$, OCH$_2$CCl$_3$), C$_{1-6}$alkylsulfonyl (e.g. SO$_2$Me, SO$_2$Et), C$_{1-6}$alkoxyC$_{1-6}$alkyl (e.g. OCH$_2$OCH$_3$, OCH$_2$OCH$_2$CH$_3$, (ICH$_2$)$_2$CH$_3$, O(CH$_2$)$_2$OCH$_2$CH$_3$, O(CH$_2$)$_3$OCH$_3$, O(CH$_2$)$_3$OCH$_2$CH$_3$, O(CH$_2$)$_2$—O—(CH$_2$)$_2$CH$_3$, O(CH$_2$)$_3$—O—(CH$_2$)$_2$CH$_3$), NH$_2$, C$_{1-6}$alkylamino (e.g. NHMe, NHEt, NHPr, NHBu), diC$_{1-6}$alkylamino (e.g. NMe$_2$, NEt$_2$, NPr$_2$), C(O)OC$_{1-6}$alkyl (e.g. C(O)OMe, C(O)OEt, C(O)OPr, C(O)OBu,), hydroxyC$_{1-6}$alkyl (e.g. CH$_2$OH, (CH$_2$)$_2$OH, (CH$_2$)$_3$OH), hydroxyC$_{1-6}$alkoxy (e.g. OCH$_2$OH, O(CH$_2$)$_2$OH, O(CH$_2$)$_3$OH), C$_{1-6}$alkyl 5-6-membered heteroaryl (e.g. methyltetrazolyl), (alkoxyacetyloxy)haloC$_{1-6}$alkyl (e.g. CH(OC(O)CH$_2$OC$_{1-6}$alkyl)CHFCH$_3$), C$_{1-6}$alkyl-sulfonylaminoC$_{1-6}$alkyl (e.g. CH$_2$NHSO$_2$Me, (CH$_2$)$_2$NHSO$_2$Me, (CH$_2$)$_2$NHSO$_2$Et).

As used herein, the term "alkyl" or "alk", used either alone or in compound words denotes straight chain, branched or cyclic alkyl, preferably C$_{1-20}$ alkyl, eg C$_{1-10}$ or C$_{1-6}$ Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butyl-heptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like. Where an alkyl group is referred to generally as "propyl", "butyl" etc, it will be understood that this can refer to any of straight, branched and cyclic or ring-containing isomers where appropriate. An alkyl group may be further optionally substituted by one or more (same or different) substituents selected from halo, hydroxy, C$_{1-6}$alkoxy, amino, C$_{1-6}$alkylamino, diC$_{1-6}$alkylamino, CO$_2$H, CO$_2$C$_{1-6}$alkyl, C(O)C$_{1-6}$alkyl and thus, as used herein, is taken to include optionally substituted alkyl.

The term "alkenyl" as used herein denotes groups formed from straight chain, branched or cyclic hydrocarbon residues containing at least one carbon to carbon double bond including ethylenically mono-, di- or poly-unsaturated alkyl or cycloalkyl groups as previously defined, preferably C$_{2-20}$ alkenyl (eg C$_{2-10}$ or C$_{2-6}$). Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

As used herein the term "alkynyl" denotes groups formed from straight chain, branched or cyclic hydrocarbon residues containing at least one carbon-carbon triple bond including ethynically mono-, di- or poly-unsaturated alkyl or cycloalkyl groups as previously defined. Unless the number of carbon atoms is specified the term preferably refers to C$_{2-20}$ alkynyl (eg C$_{2-10}$ or C$_{2-6}$). Examples include ethynyl, 1-propynyl, 2-propynyl, and butynyl isomers, and pentynyl isomers.

The term "carbocyclyl" includes any of non-aromatic monocyclic, polycyclic, fused or conjugated hydrocarbon residues, preferably C$_{3-20}$ (eg C$_{3-10}$ or C$_{3-8}$). The rings may be saturated, eg cycloalkyl, or may possess one or more double bonds (cycloalkenyl) and/or one or more triple bonds (cycloalkynyl). Particularly preferred carbocyclyl are 5-6-membered or 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl, indanyl, decalinyl and indenyl.

The term "heterocyclyl" when used alone or in compound words includes any of monocyclic, polycyclic, fused or conjugated hydrocarbon residues, preferably C$_{3-20}$ (eg C$_{3-10}$ or C$_{3-8}$) wherein one or more carbon atoms are replaced by a heteroatom so as to provide a non-aromatic residue. Suitable heteroatoms include, O, N, S, P and Se, particularly O, N and S. Where two or more carbon atoms are replaced, this may be by two or more of the same heteroatom or by different heteroatoms. The heterocyclyl group may be saturated or partially unsaturated, ie possess one or more double bonds. Particularly preferred heterocyclyl are 5-6 and 9-10 membered heterocyclyl. Suitable examples of heterocyclyl groups may include pyrrolidinyl, pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, pyranyl and dihydropyranyl.

The term "acyl" either alone or in compound words denotes a group containing the moiety C=O (and not being a carboxylic acid, ester or amide) Preferred acyl includes C(O)—R, wherein R is hydrogen or an alkyl, alkenyl, alkynyl, aryl, heteroaryl, carbocyclyl, or heterocyclyl residue. Examples of acyl include formyl, straight chain or branched alkanoyl (eg. C$_{1-20}$) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and naphthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. The R residue may be optionally substituted as described herein. Accordingly, "acyl" is also taken to refer to optionally substituted acyl.

The term, "amino" is used here in its broadest sense as understood in the art and includes groups of the formula $NR^AR^B$ wherein $R^A$ and $R^B$ may be any independently selected from hydrogen, alkyl, alkenyl, alkynyl, aryl, carbocyclyl, hateroary, heterocyclyl, aralkyl, and acyl. $R^A$ and $R^B$, together with the nitrogen to which they are attached, may also form a monocyclic, or polycyclic ring system eg a 3-10 membered ring, particularly, 5-6 and 9-10 membered systems. Examples of "amino" include $NH_2$, NHalkyl (eg $C_{1-20}$alkyl), NHaryl (eg NHphenyl), NHaralkyl (eg NHbenzyl), NHacyl (eg $NHC(O)C_{1-20}$alkyl, NHC(O)phenyl), Nalkylalkyl (wherein each alkyl, for example $C_{1-20}$, may be the same or different) and 5 or 6 membered rings, optionally containing one or more same or different heteroatoms (eg O, N and S). The term [group]amino, such as "alkylamino" or "dialkylamino", is intended to reflect the nature of the $R^A$ and $R^B$ groups.

The term "amido" is used here in its broadest sense as understood in the art and includes groups having the formula $C(O)NR^AR^B$, wherein $R^A$ and $R^B$ are as defined as above. Examples of amido include $C(O)NH_2$, C(O)NHalkyl (eg $C_{1-20}$alkyl), C(O)NHaryl (eg C(O)NHphenyl), C(O)NHaralkyl (eg C(O)NHbenzyl), C(O)NHacyl (eg $C(O)NHC(O)C_{1-20}$alkyl, C(O)NHC(O)phenyl), C(O)Nalkylalkyl (wherein each alkyl, for example $C_{1-20}$, may be the same or different) and 5 or 6 membered rings, optionally containing one or more same or different heteroatoms (eg O, N and S).

The term "carboxy ester" is used here in its broadest sense as understood in the art and includes groups having the formula $CO_2R$, wherein R may be selected from groups including alkyl, alkenyl, alkynyl, aryl, carbocyclyl, heteroaryl, heterocyclyl, aralkyl, and acyl. Examples of carboxy ester include $CO_2C_{1-20}$alkyl, $CO_2$aryl (eg. $CO_2$phenyl), $CO_2$aralkyl (eg $CO_2$ benzyl).

As used herein, "heteroatom" refers, in its broadest sense, to any atom other than a carbon atom which may be a member of a cyclic organic compound. Examples of suitable heteroatoms include nitrogen, oxygen, sulfur, phosphorous, boron, silicon, arsenic, sellenium and telluruim, more preferably, nitrogen, oxygen and sulfur.

Terms written as "[group]oxy" refer to a particular group when linked by oxygen, for example, the terms "alkoxy", "alkenoxy", "alkynoxy" and "aryloxy" and "acyloxy" respectively denote alkyl, alkenyl, alkynyl, aryl and acyl groups as hereinbefore defined when linked by an oxygen atom. Terms written as "[group]thio" refer to a particular group when linked by sulfur, for example, the terms "alkylthio", "alkenylthio", alkynylthio" and "arylthio" respectively denote alkyl, alkenyl, alkynyl, aryl groups as hereinbefore defined when linked by a sulfur atom. Similarly, a term written as "[groupA]groupB" is intended to refer to a groupA when linked by a divalent form of groupB, for example, "hydroxyalkyl" is a hydroxy group when linked by an alkylene group.

The term "halogen" ("halo") denotes fluorine, chlorine, bromine or iodine (fluoro, chloro, bromo or iodo).

It will be understood that the invention also encompasses agriculturally acceptable salts and esters, as well as metabolic products thereof. It will be appreciated that tautomeric forms, where appropriate, are also intended to be encompassed by the invention.

Sulfonylurea compounds may also be classified according to the nature of an aryl or heteroaryl group attached to the sulfonlyurea moiety, for example, in triazinylsulfonylurea compounds the terminal N atom of the urea moiety is attached to an optionally substituted triazinyl group, and in pyrimidinysulfonylureal compounds the terminal N atom of the urea moiety is attached to an optionally substituted pyrimidinyl group. Thus, in one embodiment of the invention, the sulfonylurea compound, or its agriculturally acceptable salt or ester thereof is a triazinylsulfonylurea or a pyrimidinylsulfonylurea.

Some particular examples of the pyrimidinylsulfonylurea compounds include: amidosulfuron, azimsulfuron, benzulfuron, chlorimuron, cyclosulfamuron, ethoxysulfuron, flazasulfuron, flucetosulfuron, flupyrsulfuron, halosulfuron imazosulfuron, mesosulfuron, nicosulfuron, orthosulfamuron, oxasulfuron, primisulfuron, pyrazosulfuron, rimsulfuron, sulfometuron, sulfosulfuron, and trifloxysulfuron. Some examples of the triazinylsulfonylurea compounds include: chlorsulfuron, cinosulfuron, ethametsulfuron, iodosulfuron, metsulfuron, prosulfuron, thifensulfuron, triasulfuron, tribenuron, triflusulfuron and tritosulfuron, and their agriculturally acceptable salts and esters.

Some particularly preferred examples of sulfonylurea compounds contemplated by the present invention are metsulfuron-methyl, triasulfuron, mesosulfuron-methyl, thifensulfuron and sulfosulfuron as illustrated below.

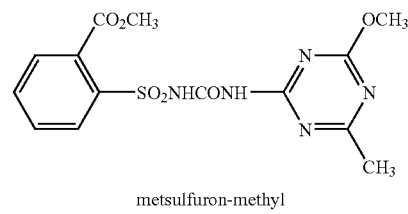

metsulfuron-methyl

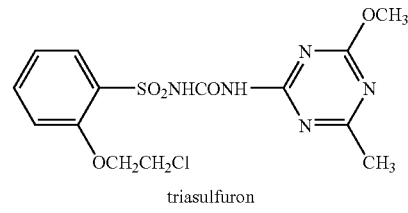

triasulfuron

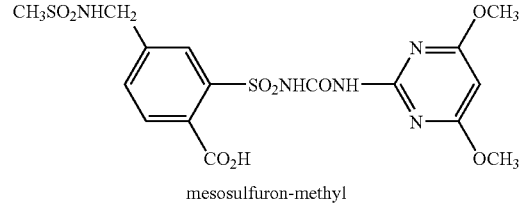

mesosulfuron-methyl

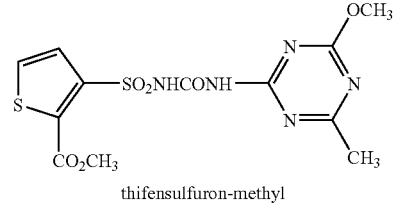

thifensulfuron-methyl

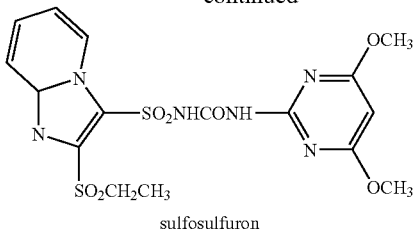
sulfosulfuron

These compounds, known for their herbicidal properties, are available as commercial formulations which may be used in the present invention. An example of commercial formulation of metsulfuron-methyl is Brush Off™, which is manufactured by DuPont. An example of a commercial formulation of mesosulfuron-methyl is Atlantis™ which is manufactured by Bayer Crop Science. A commercial formulation of triasulfuron is Logran™ which is manufactured by Syngenta. Thifensulfuron methyl is commercially available under the name Harmony™ (DuPont) and sulfosulfuron is available under the name Monza™ (Monsanto).

The term "poppy plant" refers to the *Papaver somniferum* plant as well as any part of a *Papaver somniferum* plant including, but not limited to roots, bud, stem, seed, capsules, flowers, and leaves. It will be understood that unless the context indicates otherwise, reference to the singular term as used herein also includes a plurality of plants, eg a poppy crop, and that singular and plural forms may be used interchangeably.

The term "morphine crop" or "morphine variety" encompasses a plant or strain of poppy wherein the amount of morphine and codeine produced is greater than the amount of thebaine and oripavine.

The term "thebaine crop" or "thebaine variety" encompasses a plant or strain of poppy wherein the amount of morphine and codeine produced is less than the amount of thebaine and oripavine.

Poppy plants are normally grown from seed until they mature to produce capsules. Once the plant has matured, the capsules and a part of the stem are harvested. After the seeds are collected for culinary use the deseeded capsules and stem (together known as "straw") are processed in order to extract the alkaloids.

The term "alkaloid" or "alkaloids" encompasses a class of organic compounds containing nitrogen, isolated from plants, particularly poppy plants, and includes thebaine and/or oripavine and/or neopinone and/or, codeinone and/or morphinone and/or codeine and/or morphine and/or noscapine, and/or papaverine. Preferably, the alkaloid is selected from one or more of the group consisting of morphine, thebaine and oripavine, particularly morphine or thebaine. The most valuable part of the plant is the capsule containing the majority of the total plant alkaloids. Stems and other parts of the plant also contain the alkaloids although in lower concentration.

The term "alkaloid yield" refers to the amount of alkaloid theoretically obtainable from the capsule and/or stem of a poppy plant. The term "alkaloid recovery" is the amount of alkaloid actually recovered from poppy plant by methods of extraction and/or harvesting. It will be appreciated that the amount of alkaloid recovered may not equal the alkaloid yield because alkaloid could be lost or reduced through the process of extraction and/or harvesting. Alkaloid yield and/or recovery is indicated in the Examples by the parameters "straw morphine/thebaine %" and "morphine/thebaine kg/ha". Various factors can influence alkaloid recovery and/or yield. For example, plant height, lodging, and capsule weight all affect alkaloid recovery.

The term "plant height", when referring to a poppy plant, refers to the height of the poppy plant as determined by the length of the stem. Thus, reducing poppy plant height is equivalent to reducing stem height. If plant height is reduced, then a greater capsule to stem ratio can be achieved in a given amount of poppy straw. This is due to less stem being cropped by harvesting techniques. Therefore the straw contains a greater proportion of capsule (which contains most of the alkaloid) to stem.

The term "lodging" refers to the permanent displacement of a stem from its normal position. Displacement can range from a slight or small change in the normal position of the stem to a more extreme effect where the stem has fallen close to or to the ground. If lodging is reduced then alkaloid is less likely be lost or reduced through leaching out onto the ground from capsules falling to or close to the ground. Thus, a decrease in lodging may result in an increase in alkaloid recovery. Lodging is measured herein as a % of plants in a crop in which the stem is permanently displaced from its normal position.

The term "seed weight" refers to the weight of the seed per poppy plant. If seed weight is reduced, this results in an increased capsule to seed ratio which could result in increased alkaloid yield and/or recovery from the capsule. Without wishing to limit the invention, an increase in alkaloid yield could occur as a result of more energy being available and redirected from the production of seed into the production of the capsule. Thus, if a bigger capsule is produced more alkaloid per capsule may also be produced, thereby potentially increasing alkaloid yield and/or recovery.

"Capsule weight" includes reference to the amount of capsule compared to stem and/or seeds. It may be expressed as a weight quantity or as a proportional measure, for example, as the weight of capsule in a given amount of straw or capsule to seed ratio. Increasing capsule weight is potentially beneficial in that it may increase the alkaloid yield and/or recovery from a poppy plant.

The term "straw" or "poppy straw" encompasses mature or ripe (dry) poppy capsules and stems which have been treated to remove the seeds, and thus form a straw. "Straw weight" is defined as the weight of the capsule and stem. "Capsule weight" in this regard can be considered as the weight of capsule in a given amount of straw. Thus, increasing straw weight by increasing capsule weight is potentially beneficial in that it may increase the amount of alkaloid recoverable from a given weight of straw. An increase in "straw weight" in the examples mainly reflects an increase in capsule weight in straw.

The term "concentrate of poppy straw" includes the material arising when poppy straw has entered into a process for the concentration of its alkaloids, when such material is made available in trade, (Multilingual Dictionary Of Narcotic Drugs And Psychotropic Substances Under International Control, United Nations, New York, 1983). Not inconsistent with the foregoing definition, concentrate of poppy straw is defined as "the crude extract of poppy straw in either liquid, solid or powder form which contains the phenanthrene alkaloids of the opium poppy," 45 U.S. Federal Register 77466, Nov. 24, 1980. When in liquid form, the liquid is preferably concentrated before entering into commerce. The generally preferred concentrate of poppy straw is the powder form which results from simply removing the solvent or water following extraction of the poppy straw.

The term "opium" encompasses the air dried latex or the milky exudate obtained by incision of the immature or unripe (green) capsule of a poppy plant. To harvest opium, the skin of the ripening pods is scored by a sharp blade. The slashes exude a white, milky latex, which dries to a sticky brown resin that is scraped off the pods as raw opium. It generally contains morphine, noscapine, codeine, papaverine and thebaine (Merck Index, 6986 12th Edition).

As used throughout, the term "applying", or variations thereof such as "application", is used to mean that the poppy plant or locus thereof has contact with the described compound(s) or composition(s) thereof by application methods known in the art. As such, the compounds (or their salts or esters) of the present invention can be applied in a number of ways, for example, they can be applied (formulated or unformulated) directly to the foliage of the plant or they can be sprayed on, broadcast, dusted on or applied as a cream or paste formulation or they can be applied as slow release granules (ie by injecting, shanking, chiseling or working into the soil). Compositions may be applied in a single application, although multiple, separate or sequential applications at one or more growth stages of the compound(s) or composition(s) used in the invention are generally preferred.

Advantageously, the sulfonylurea compounds can be used in effective amounts which are amounts substantially less than those used for herbicidal activity and prefereably in amounts less than those used for other growth regulators.

An "effective amount" of a compound will vary according to the compound used, prevailing conditions such as weather, growth stage, mode and number of applications, cultivation practice and the like. In general, "effective amount" means the amount of the compound needed to achieve one or more of a detectable or observable reduction in poppy (stem) height, lodging, seed weight, or a detectable or observable increase in capsule weight in poppy straw, or preferably, an increase in alkaloid yield and/or recovery according to a desired application regime. Thus a "height reducing effective amount" is an amount of compound applied at a desired growth stage in accordance with an application regime to achieve a reduction in the height of the poppy plant. Similarly, a "lodging reducing effective amount", "seed weight reducing effective amount", "capsule increasing effective amount" or "straw weight increasing amount" is an amount of compound applied at a desired growth stage in accordance with a suitable application regime to achieve a reduction in lodging, reduction in seed weight or increase in capsule or straw weight respectively. An alkaloid yield and/or recovery increasing amount is an amount of compound which achieves an increase in the alkaloid yield and/or recovery. Where the compounds are applied in an amount or in accordance with an application regime which has a phytotoxic effect on the poppy plant, the benefits and advantages of the invention may be reduced or lost (although it will be recognised that some benefits may still be obtained even where there is some observable phytotoxicity). Accordingly, an effective amount of a compound is preferably an amount applied in accordance with an application regime which has no substantial phytotoxic effect on the plant. The skilled person can determine suitable effective amounts and application regimes by routine experimentation.

The sulfonylurea compounds are applied at rates substantially less than those used for herbicidal purposes, typically at rates of less than 1 g per hectare. Suitable rates of application of the active ingredient ("a.i.") may be in the range of from about 5 mg to about 800 mg a.i., preferably about 30 mg a.i. to about 600 mg a.i. per hectare, say from about 50 to about 550 mg a.i. per hectare. Exemplary rates include from about 100 to about 200, from about 200 to about 300 and from about 300 to about 400 mg a.i. per hectare, about 400 to 500 mg a.i. per hectare, about 500 to 600 mg a.i. per hectare and about 600 to 700 mg a.i. per hectare. Thus an a.i. may be applied once at an appropriate rate of about 5 to 800 mg a.i./ha at an appropriate growth stage or 2 or more times, each at a rate of about 5 to 800 mg a.i./ha at differing growth stages, wherein the rate at each application may be the same or different.

When the active ingredient is metsulfuron-methyl some preferable rates range from about 30 mg a.i. per hectare to about 400 mg a.i. per hectare, for example from about 50 mg a.i. to 300 mg a.i. per hectare. One exemplary application rate is in the range of from about 100 mg a.i. to about 150 mg a.i. per hectare, for example, about 120 mg a.i. per hectare.

Suitable rates of application of triasulfuron may range from about 50 mg a.i. per hectare to 600 mg a.i. per hectare. Exemplary ranges include from about 75 or 150 mg a.i. per hectare to about 300 mg a.i. per hectare, from about 300 mg a.i. per hectare to about 400 mg a.i. per hectare, from about 400 mg a.i. per hectare to about 500 mg a.i. per hectare or 550 mg a.i. per hectare. Exemplary rates include about 75 mg or 150 mg a.i. per hectare or about 263 mg a.i. per hectare or 525 mg a.i. per hectare.

Mesosulfuron-methyl may be applied at a rate of from about 150 mg to about 500 mg a.i. per hectare, such as from about 300-400 mg a.i. per hectare. Exemplary rates are about 150 or 390 mg a.i. per hectare.

Thifensulfuron methyl may be applied at a rate of up to about 50-500 mg a.i. per hectare, such as about 300-450 mg a.i. per hectare.

Sulfosulfuron may be applied at a rate of about 50-800 mg a.i. per hectare for example, about 50-200 mg a.i. per hectare or about 250-400 mg a.i. per hectare or about 450 to 650 mg a.i. per hectare. Some exemplary rates are 60, 180 and 600 mg a.i. per hectare.

The sulfonylurea compounds can be applied in one or more applications. In some preferred embodiments of the invention, the sulfonylurea compound can be applied in two or three separate applications. When the sulfonylurea compound is metsulfuron-methyl, in one preferred embodiment at least two applications of the compound are used. Even more preferable is three applications. When metsulfuron-methyl is applied alone, then three applications of 120 mg a.i. per hectare may be desirable. However, when applied with other growth regulators such as trinexapac-ethyl two applications at 120 mg a.i. per hectare may be desirable together with two applications of trinexapac ethyl at 0.5 L per hectare, and concentration 250 g a.i./L. Two applications of triasulfuron at 263 mg a.i. per hectare or one application at 525 mg a.i. per hectare are exemplary rates. Two applications of mesosulfuron-methyl at 0.39 ml/ha may be preferred. Suitable effective amounts and application regimes can be readily determined by the skilled person by routine experimentation.

"Locus thereof" refers to the general area in which the poppy plant(s) are grown to which application of compound(s) used in the invention achieve the desired effect such as altering the alkaloid composition in the poppy plant(s) or parts thereof. Thus, for example, the locus, can refer to the surrounding growth medium, eg soil, in which the plants are grown and may encompass the whole or part of the planted area. Also compounds used in the invention may also be applied to fertilizer or poppy seed and placed in the soil at sowing time. Alternatively, a jet stream of compound or chemical used in the invention may be directed at a point into the ground next to the poppy plant(s) and allowed to diffuse through the soil and be taken up by the roots of the poppy plant(s). The locus can also refer to the air surrounding the plant(s), when the compound or composition used in the invention can be applied in the form of a spray or vapour.

Desirably, the effects achieved by the invention can be measured against a control. The term "control" preferably refers to the same type, variety, or cultivar of poppy plant which has been subjected to identical conditions, bar the application of the sulfonylurea compound, although it will be recognised that under some circumstances other control conditions may be used for comparison, for example when the application of a sulfonylurea compound is compared against another growth regulator or the addition or exclusion of other active agents, and/or adjuvants. Thus, a reduction in the plant height, reduction in lodging, a reduction in seed weight, an increase in capsule weight, an increase in straw weight, or an increase in alkaloid yield or recovery refers to a detectable or observable reduction or increase, as appropriate, when compared to a plant that has not been treated with the compound or an ineffective amount thereof. It will be understood that even where one or more of a reduction in plant height, lodging or seed weight or increase in capsule weight may not be individually detected or observed, the additive effects thereof may nevertheless result in a detected or observed increase in straw weight or alkaloid yield or recovery.

During the growth from seed, poppy plants go through several developmental stages which are herein designated by the following terms: 4-6 leaf stage (early post emergent), 6-8 leaf stage, 8-10 leaf stage, 10-12 leaf stage (row cover), ground cover (12-14 leaf), run up (early and mid and late), bud emergence, bud to hook, hook and lastly flowering. Maturity and harvesting occur about 6-8 weeks post flowering. The ground cover stage is where plants have 12-14 leaves, are in a rosette habit and, as the term implies are covering the ground such that the bare ground is not easily visible when the plants have the normal row spacing of 15-20 cm. Run-up includes both early run-up and late run-up. Early run-up is the emergence of the stem from the rosettes. Late run-up is the beginning of the emergence of the buds as the stem is elongated. Clearly not all the plants in any given crop will be at the same growth stage however the terms used herein refer to the growth stage of the leaves of the majority of the plants or of the majority of primary buds once they have appeared.

The compositions for use in the present invention, comprising sulfonylurea compounds may be applied anytime up to flowering, but application during one or more of row cover, ground cover, run up, bud emergence, hook or early flowering growth stages is preferred.

When operating in accordance with the present invention, the poppy plants or area proximate to the poppy plants is contacted with an effective amount of the compound or composition of the present invention. The application of such compositions to terrestrial plants can be carried out by conventional methods, e.g. power dusters, boom and hand sprayers and spray dusters.

As noted above, the sulfonylurea compounds may be applied as salts, particularly agriculturally acceptable salts.

The term "agriculturally acceptable salts" includes cationic or anionic salts which are known and accepted in the art for agricultural or horticultural use. Preferably the salts are water-soluble. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts, formed by compounds containing an nitrogen atom with an available lone pair, include salts with inorganic acids, for example hydrochlorides, sulfates, phosphates and nitrates and salts with organic acids, for example acetic acid. Suitable metal and alkaline earth metal hydroxides as salt formers include the salts of barium, aluminum, nickel, copper, manganese, cobalt zinc, iron, silver, lithium, sodium, potassium, magnesium or calcium. Additional salt formers include chloride, sulfate, metrab, acetate, carbonate, hydride, and hydroxide. Methods for forming salts are well known.

Free carboxylic acid and hydroxy groups may be converted into their corresponding (agriculturally acceptable, ie non-detrimental for the desired agricultural purpose) esters, such as alkyl (eg methyl, ethyl or propyl) esters and 3-6-membered heterocyclyl esters (eg oxetanyl, tetrahydrofuranyl, piperidinyl, pyrrolidinyl). Methods for esterifying carboxylic acids and hydroxy groups (acylating) are well known in the art.

Sulfonylurea compounds used in the present invention may be applied unformulated or formulated into a composition. Preferably the compounds are applied in the form of a composition comprising the sulfonylurea compound and one or more agriculturally acceptable additives and/or active ingredients.

Compositions for use in the invention may contain a carrier. The carrier may be any natural or synthetic organic or inorganic ingredient that facilitates dispersion of the composition or compound and contact with the plant. The carrier may be solid (e.g. clays, synthetic silicates, silica, resins, waxes, kaolin, bentonite, dolomite, calcium carbonate, talc, powdered magnesia, Fuller's earth, gypsum, diatomaceous earth, China clay, lime and combinations thereof); liquid (e.g. water, aqueous solutions, N-methylpyrrolidone, kerosene, cyclohexanone, methylethyl ketone, acetonitrile, methanol, ethanol, isopropyl alcohol, acetone, butyl cellosolved, 2-ethyl-lhexanol, cyclohexanone, methyl cellulose, polyvinyl alcohol, sodium lignin sulfonates, polymeric alkyl naphthalene sulfonates, sodium naphthalene sulfonate, polymethylene bisnaphthalenesulfonate, sodium N-methyl-N-(long chain acid) laureates, hydrocarbons and other water-immiscible ethers, esters and ketones, and combinations thereof); or a combination of solid and liquid carriers.

Compositions useful in the present invention may also contain one or more surfactants to increase the biological effectiveness of the active ingredient. Suitable surface active ingredients include surfactants, emulsifying agents, and wetting agents. A wide range of surfactants is available and can be selected readily by those skilled in the art from "The Handbook of Industrial Surfactants," 2nd Edition, Gower (1997), which is incorporated herein by reference in its entirety for all purposes. There is no restriction on the type or chemical class of surfactant(s) that can be used. Nonionic, anionic, cationic and amphoteric types, or combinations of more than one of these types, may all be useful in particular situations.

Among nonionic surfactants, exemplary classes may include polyoxyethylene alkyl, alkyne, alkynyl or alkylaryl ethers, such as polyoxyethylene primary or secondary alcohols, alkylphenols or acetylenic diols; polyoxyethylene alkyl or alkyne esters, such as ethoxylated fatty acids; sorbitan alkylesters, whether ethoxylated or not; glyceryl alkylesters; sucrose esters; and alkyl polyglycosides. Exemplary anionic surfactant classes include fatty acids, sulfates, sulfonates, and phosphate mono- and diesters of alcohols, alkylphenols, polyoxyethylene alcohols and polyoxyethylene alkylphenols, and carboxylates of polyoxyethylene alcohols and polyoxyethylene alkylphenols. These can be used in their acid form but are more typically used as salts, for example sodium, potassium or ammonium salts.

Cationic surfactants classes may include polyoxyethylene tertiary alkylamines or alkenylamines, such as ethoxylated fatty amines, quaternary ammonium surfactants and polyoxyethylene alkyletheramines. Representative specific examples of such cationic surfactants include polyoxyethylene (5) cocoamine, polyoxyethylene (15) tallowamine, distearyldimethylammonium chloride, N-dodecylpyridine chloride and polyoxypropylene (8) ethoxytrimethylammonium chloride. Many cationic quaternary ammonium surfactants of diverse structures are known in the art to be useful in combination with herbicides and can be used in compositions contemplated herein.

Suitable emulsifying agents and wetting agents may include, but are not limited to, ionic and nonionic types such as polyacrylic acid salts, lignosulphonic acid salts, phenolsulphonic or naphthalenesulphonic acids, products of polycondensation of ethylene oxide with fatty alcohols, fatty acids or fatty amines, substituted phenols (especially alkylphenols or arylphenols), sulphonosuccinic acid ester salts, taurine derivatives (especially alkyl taurates), phosphoric esters of alcohols or products of polycondensation of ethylene oxide with phenols, esters of fatty acids with polyhydric alcohols, and derivatives having sulphate, sulphonate and phosphate groups, of the compounds above.

The methods of the invention may also be used in conjunction with the application of other active agents, for example fertilizers such as ammonium nitrate, urea, potash, and superphosphate; phytotoxicants and plant growth regulators; trinexapac ethyl; safeners; fungicides; pesticides and other alkaloid altering compositions such as thidiazuron or clopyralid. These additional agents may be used in combination (either together, separately or sequentially) with the above-described compositions. Thus, compositions used in the invention may also contain one or more active agents. Alternatively, the poppy plant(s) may be treated with other active agents before or after applying the sulfonylurea compound. Alternatively, a separate composition containing the active agent may be applied concurrently. In one preferred embodiment, the sulfonylurea compound is applied in combination with a trinexapac ethyl.

Other optional components may be admixed with the present compositions to facilitate the application and/or effectiveness of the active ingredient. To this end, optional components that may be added include antifoaming agents including silicone based antifoaming agents; thickening agents such as fumed silica; antimicrobial agents; antioxidants; buffers; dyes; perfumes; stabilizing agents; and antifreezing agents. Exemplary antifreezing agents include but are not limited to, glycols such as propylene glycol and ethylene glycol, N-methylpyrrolidone, cyclohexanone, and alcohols such as ethanol and methanol.

The compounds used in the present invention may be present in any effective formulation, including, but not limited to dusting powders or granules; dispersible powders, granules or grains; pellets, aqueous dispersions; emulsions or micro-encapsulation.

Powders, including dusting powders or granules and dispersible powders, granules or grains contain at least one active ingredient and an inert solid extender or carrier, such as kaolin, bentonite, dolomite, calcium carbonate, talc, powdered magnesia, Fuller's earth, gypsum, diatomaceous earth and China clay. Dispersible powders, granules and grains typically also include one or more wetting and dispersing agents, such as surfactants.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agents(s). Suitable organic solvents are kerosene, cyclohexanone, methylethyl ketone, acetone, methanol, acetonitrile, and the like. The compositions may also be in the form of liquid preparations for use as dips or sprays which are generally aqueous dispersions or emulsions containing the active ingredient in the presence of one or more of wetting agent(s), dispersing agent(s), emulsifying agent(s) or suspending agent(s).

Typical liquid solutions include the active ingredient, a carrier, and optionally, a surface active agent. The dilute solutions of the present compositions generally contain about 0.1 to about 50 parts active ingredient, about 0.25 to about 50 parts carrier, and about 0 to about 94 parts surface active agent, all parts being by weight based on the total weight of the composition. Similarly, the concentrated compositions typically include about 40 to about 95 parts active ingredient, about 5 to about 25 parts carrier, and about 0 to about 20 parts surface active agent.

Emulsions are usually solutions of active ingredients in water-immiscible or partially water-immiscible solvents as the carrier together with at least one surface active agent. Suitable solvents for the active ingredients of this invention include, but are not limited to, hydrocarbons and water-immiscible ethers, esters or ketones. The emulsification compositions generally contain from 5 to 95%, preferably 20 to 70% by weight of the active compound of this invention as active ingredient; 1 to 40%, preferably 5 to 20% by weight of surfactant; and 4 to 94%, preferably 10 to 75% by weight of liquid carrier.

The compositions may be prepared in a known manner, for example by homogeneously mixing or grinding the active ingredients with other ingredients. Additional components may be admixed with the composition at any point during the process, including during and/or after any mixing.

The present invention is further described by the following non-limiting Examples which are included for the purpose of illustrating certain embodiments of the invention and are not intended to limit the generality hereinbefore described.

General Methods Used in Examples

All trials were conducted on poppy crops. Seed was treated with Thiram (5.6 g of Thiram 800/kg seed) and Apron (4 g/kg) and sown at a rate of approximately 750 g/ha. Fertilisers were applied at sowing. Most commonly, either 50:50 lime:superphosphate/triple superphosphate at 125 kg/ha, or lime:superphosphate at 250 kg/ha, were mixed with seed and drilled at a depth of 15 mm. In the same operation, NPK (nitrogen:phosphorus:potassium), at various rates, was banded 75 mm below the seed, unless otherwise stated. All crops were subjected to herbicide sprays for weed control, fungicide sprays for disease control, insecticide sprays if appropriate and were irrigated as required.

All spray applications were made with a precision sprayer, using Silvan Lurmark flat-fan, low-drift nozzles (LD110-0015). Spray equipment was calibrated to deliver 153 L water/ha.

At harvest, a 2 m×4 m quadrat was placed in each plot (3 m×6 m, unless otherwise stated) and capsules hand-picked from this area. Capsules were broken up, seed and capsule material separated and weighed. Capsule moisture readings were taken with a moisture meter. Alkaloid yield data were calculated on Pesticide Research Manager (version 5 for Windows) using the formulae below. Briefly, capsule weight was adjusted for moisture to a dry weight, 5% of seed weight was added to this (this amount of capsule material regularly occurs in seed samples after processing) to give a capsule weight per plot. Seed weight was adjusted to 95% of crude weight. Straw weights were determined by multiplying dry capsule weight by 1.3 (estimated amount of stem material in a commercial harvest) and adjusted to 11% moisture. When Lontrel was applied to crops exact capsule and seed weight data were entered. Analyses of variance and a Multiple Range Test were performed on data using Pesticide Research Manager. Significant differences (P=0.05) between treatments are denoted by different lower case letters adjacent to treatment means in the tables of results.

| CALCULATION OF CROP PARAMETERS | | |
|---|---|---|
| [1] | Seed weight (unadjusted) g/plot (8 m$^2$) | |
| [2] | Capsule weight (unadjusted) g/plot (8 m$^2$) | |
| [3] | Moisture (%) | |
| [4] | Dry capsule weight (unadjusted) g/plot (8 m$^2$) formula 1: [2] − (([2] * [3])/100) | |
| [5] | 5% seed weight (unadjusted) g/plot (8 m$^2$) formula 2: [1] * 0.05 | |
| [6] | Dry 5% extra capsule weight g/plot (8 m$^2$) formula 3: [5] − (([5] * [3])/100) | |
| [7] | Dry capsule weight (adjusted) g/plot (8 m$^2$) formula 4: [4] + [6] | |
| [8] | Seed weight (adjusted) g/plot (8 m$^2$) formula 5: [1] − [5] | |
| [9] | Total weight (adjusted) g/plot (8 m$^2$) formula 6: [7] + [8] | |
| [10] | Capsule:seed ratio formula 7: [7]/[8] | |
| [11]# | Straw weight kg/ha formula 8: [7] * 1.11 * 1.3 * 1.25 | |
| [12]# | Seed weight kg/ha formula 9: [8] * 1.25 | |
| [13] | Crop weight t/ha formula 10: ([11] + [12])/1000 | |
| [14] | Capsule morphine assay (anhydrous) % | |
| [15] | Capsule morphine assay (11% moisture) formula 11: [14] * 0.89 | |
| [16] | Stem morphine assay (11% moisture) formula 12: [14] * 0.89 * 0.115 | |
| [17] | Straw morphine (11% moisture) % formula 13: ([15] * 0.75) + ([16] * 0.25) | |
| [18] | Morphine kg/ha formula 14: ([11] * [17])/100 | |
| [19] | Capsule thebaine assay (anhydrous) % | |
| [20] | Capsule thebaine assay (11% moisture) formula 15: [19] * 0.89 | |
| [21] | Stem thebaine assay (11% moisture) formula 16: [19] * 0.89 * 0.267 | |
| [22] | Straw thebaine (11% moisture) % formula 17: ([20] * 0.75) + ([21] * 0.25) | |
| [23] | Thebaine kg/ha formula 18: ([11] * [22])/100 | |

(Explanation of terms 1.11, 1.3, and 1.25 in formulae [11 and 12]
1.11 = amount to convert dry straw to straw at 11% moisture
1.3 = amount required to convert capsule weight to capsule + (10 cm) stem weight
1.25 = conversion from g/plot (4 m$^2$) to kg/ha).

Generally, the following Examples 1-19 involved the testing of Brush-Off™ (600 g/kg metsulfuron-methyl), in association with other growth regulators. In each example, the actual amount of active ingredient per hectare is referred to as the rate (eg. 120 mg/ha metsulfuron-methyl), which is 0.2 g/ha Brush-Off™. In Examples 9 and 10, two other sulfonylurea herbicides, Atlantis™ and Logran™, respectively, were evaluated. They are referred to by their active ingredients (30 g/L mesosulfuron-methyl (Compound 2)+90 g/L mefenpyr-diethyl, a crop safener in Atlantis™, and 750 g/kg triasulfuron (Compound 3) in Logran™). In Examples 16-18, Compounds 2 and 3 are compared to Compound 1. In Example 19, two further compounds, Compound 4 (Harmony™-750 g/kg thifensulfuron-methyl) and Compound 5 (Monza™-750 g/kg sulfosulfuron) were evaluated. Other growth regulators are referred to by their trade names, and application rates for these are product/ha. They are Lontrel™ (300 g/L clopyralid), Moddus™ (250 g/L trinexapac-ethyl), Provide™ (20 g/L gibberellins $A_4$ and $A_7$) and Sunny™ (50 g/L uniconazole-p). Other agents referred to are the adjuvants Activator™ (850 g/L polyoxethylene ether and free fatty acids, 50 g/L isopropanol), Pulse™ (1020 g/L modified poly dimethyl siloxane), Hasten™ (esterified seed oil+surfactants), Spraytech™ Oil (803 g/L emulsifiable vegetable oil) and Swift™ (780 g/L alkylaryl polyoxyethylene glycol phosphate ester). Full product details are outlined below. Treatments labelled as "OTHER" (Examples 2, 4 and 8) do not relate to the present invention but are merely presented for statistical completeness since their data were included in the original statistical analyses.

| Name of compound | Active Ingredient | Formulation | Manufacturer/ Distributor |
|---|---|---|---|
| Sulfonylurea Compounds | | | |
| Compound 1 (Brush-Off ™) | 600 g/kg metsulfuron-methyl | WG | Du Pont |
| Compound 2 (Atlantis ™) | 30 g/L mesosulfuron-methyl | EC | Bayer CropScience |
| Compound 3 (Logran ™) | 750 g/kg triasulfuron | WG | Syngenta |
| Compound 4 (Harmony ™) | 750 g/kg thifensulfuron-methyl | WG | DuPont |
| Compound 5 (Monza ™) | 750 g/kg sulfosulfuron | WG | Monsanto |
| Growth Regulators | | | |
| Lontrel ™ | 300 g/L clopyralid | Liquid | DowAgro-Sciences |
| Moddus ™ | 250 g/L trinexapac-ethyl | EC | Syngenta |
| Provide ™ | 20 g/L gibberellins $A_4$ and $A_7$ | Liquid | Abbott |
| Sunny ™ | 50 g/L uniconazole-p | SC | Sumitomo |

-continued

| Name of compound | Active Ingredient | Formulation | Manufacturer/ Distributor |
|---|---|---|---|
| Adjuvants | | | |
| Activator ™ | 850 g/L alkyl polyoxyethylene ether and free fatty acids, 50 g/L isopropanol | Liquid | Nufarm |
| Hasten ™ | Esterified seed oil + surfactants | Liquid | Victorian Chemicals |
| Pulse ™ | 1000 g/L modified polydimethylsiloxane | Liquid | Monsanto |
| Spraytech Oil ™ | 803 g/L emulsifiable vegetable oil | Liquid | Spraytech |
| Swift ™ | 780 g/L alkylaryl polyoxyethylene glycol phosphate ester | Liquid | Lefroy Valley |

EXAMPLE 1

Metsulfuron-methyl (Compound 1) was applied at a rate of 36 or 120 mg/ha at 12-14 leaf and ground cover growth stages, in a morphine crop.

TABLE 1

| | Rating Unit | | | CAPSULE/ | | CROP | | | |
|---|---|---|---|---|---|---|---|---|---|
| Treatment | Rate | Rate Unit | Growth Stage | SEED RATIO | STRAW kg/ha | SEED kg/ha | WEIGHT t/ha | STRAW MORPHINE % | MORPHINE kg/ha |
| Nil | | | | 0.617 | 1735 | 1948 | 3.68 | 1.30 | 22.56 |
| Compound 1 | 36 | MG/HA | 12-14LF | 0.603 | 1757 | 2020 | 3.78 | 1.38 | 24.25 |
| Compound 1 | 120 | MG/HA | 12-14LF | 0.673 | 1660 | 1710 | 3.37 | 1.47 | 24.40 |
| Nil | | | | 0.547 | 1689 | 2138 | 3.83 | 1.36 | 22.97 |
| Compound 1 | 120 | MG/HA | GC | 1.253 | 1999 | 1105 | 3.10 | 1.31 | 26.19 |

EXAMPLE 2

Trial to compare the efficacy of 120 mg/ha metsulfuron-methyl (Compound 1) with two application rates, 1 L/ha and 2 L/ha (50 g/ha and 100 g/ha) of a known growth regulator, Sunny (uniconazole-p), in a morphine crop. Treatments were applied to crop at 10-12 leaf stage. Plant heights were measured at early hook stage.

TABLE 2

| | Rating Unit | | | | PLANT | CAPSULE/ | | | | | |
|---|---|---|---|---|---|---|---|---|---|---|---|
| Trt No | Treatment Name | Rate | Rate Unit | Grow Stg | HEIGHT cm | SEED RATIO | STRAW kg/ha | SEED kg/ha | YIELD t/ha | STRAW MORPHINE % | MORPHINE kg/ha |
| 1 | NIL | | | | 84 b | 0.691 bc | 1374 bc | 1405 a | 2.78 ab | 2.34 a | 32.05 bc |
| 2 | SUNNY | 1 | L/HA | 10-12LF | 69 c | 0.767 ab | 1574 ab | 1412 a | 2.98 ab | 2.35 a | 37.22 ab |
| 2 | ACTIVATOR | .125 | % V/V | 10-12LF | | | | | | | |
| 3 | SUNNY | 2 | L/HA | 10-12LF | 48 d | 0.868 a | 1722 a | 1367 a | 3.09 ab | 2.37 a | 40.73 a |
| 3 | ACTIVATOR | .125 | % V/V | 10-12LF | | | | | | | |
| 4 | OTHER | | | 10-12LF | 92 a | 0.627 c | 1268 c | 1408 a | 2.68 b | 2.37 a | 30.08 c |
| 5 | COMPOUND 1 | 120 | MG/HA | 10-12LF | 67 c | 0.883 a | 1255 c | 1015 b | 2.27 c | 2.09 b | 26.32 c |
| 5 | PULSE | .2 | % V/V | 10-12LF | | | | | | | |
| LSD (P = .05) | | | | | 7.957 | 0.1180 | 246.9 | 174.0 | 0.356 | 0.147 | 5.646 |
| Std Deviation | | | | | 5.774 | 0.0856 | 179.1 | 126.2 | 0.258 | 0.107 | 4.097 |
| CV | | | | | 8.02 | 11.16 | 12.45 | 9.55 | 9.36 | 4.62 | 12.31 |

EXAMPLE 3

Trial to evaluate metsulfuron-methyl (Compound 1) (120 mg/ha) applied alone, or tank-mixed with Sunny (1 L/ha=50 g/ha), in a morphine crop. Treatments were applied to crop at early-mid run-up, plant heights were measured at green capsule stage.

TABLE 3

| Trt No | Treatment Name | Rate | Rate Unit | Grow Stg | PLANT HEIGHT cm | CAPSULE/ SEED RATIO | CROP STRAW kg/ha | SEED kg/ha | WEIGHT t/ha | STRAW MORPHINE % | MORPHINE kg/ha |
|---|---|---|---|---|---|---|---|---|---|---|---|
| 1 | NIL | | | | 104.6 a | 0.557 c | 744 b | 947 ab | 1.69 ab | 2.26 a | 16.98 a |
| 2 | COMPOUND 1 | 120 | MG/HA | E-MRU | 101.0 a | 0.984 ab | 884 ab | 640 c | 1.52 ab | 2.36 a | 20.88 a |
| 2 | PULSE | .2 | % V/V | E-MRU | | | | | | | |
| 3 | COMPOUND 1 | 120 | MG/HA | E-MRU | 78.2 b | 1.171 a | 829 ab | 530 c | 1.36 b | 2.21 ab | 18.43 a |
| 3 | SUNNY | 1 | L/HA | E-MRU | | | | | | | |
| 3 | HASTEN | .5 | % V/V | E-MRU | | | | | | | |
| 4 | COMPOUND 1 | 120 | MG/HA | E-MRU | 80.6 b | 0.901 b | 939 a | 727 bc | 1.67 ab | 2.22 ab | 20.91 a |
| 4 | SUNNY | 1 | L/HA | E-MRU | | | | | | | |
| 4 | PULSE | .2 | % V/V | E-MRU | | | | | | | |
| 5 | SUNNY | 1 | L/HA | E-MRU | 78.0 b | 0.600 c | 886 ab | 1044 a | 1.93 a | 2.09 b | 18.24 a |
| 5 | ACTIVATOR | .125 | % V/V | E-MRU | | | | | | | |
| LSD (P = .05) | | | | | 6.61 | 0.2014 | 162.5 | 247.5 | 0.388 | 0.144 | 1.363 |
| Standard Deviation | | | | | 4.80 | 0.1447 | 116.7 | 177.8 | 0.278 | 0.102 | 3.082 |
| CV | | | | | 5.42 | 17.18 | 13.63 | 22.86 | 17.04 | 4.58 | 16.15 |

EXAMPLE 4

Trial to evaluate metsulfuron-methyl (Compound 1) (120 mg/ha) alone, or tank-mixed with Sunny (1 L/ha), in a morphine crop. Treatments were applied to crop at early run-up, plant heights were measured at early green capsule stage.

TABLE 4

| Trt No | Treatment Name | Rate | Rate Unit | Grow Stg | PLANT HEIGHT cm | CAPSULE/ SEED RATIO | STRAW kg/ha | SEED kg/ha | CROP WEIGHT t/ha | STRAW MORPHINE % | MORPHINE kg/ha |
|---|---|---|---|---|---|---|---|---|---|---|---|
| 1 | NIL | | | | 86.6 a | 0.639 c | 1238 ab | 1341 a | 2.58 a | 2.34 a | 28.88 ab |
| 2 | COMPOUND 1 | 120 | MG/HA | ERU | 82.6 a | 0.978 a | 1349 a | 955 c | 2.30 b | 2.32 a | 31.32 a |
| 2 | PULSE | .2 | % v/v | ERU | | | | | | | |
| 3 | COMPOUND 1 | 120 | MG/HA | ERU | 73.0 c | 0.773 b | 1141 bc | 1027 c | 2.17 b | 2.43 a | 27.67 bc |
| 3 | SUNNY | 1 | L/HA | ERU | | | | | | | |
| 3 | PULSE | .2 | % V/V | ERU | | | | | | | |
| 4 | SUNNY | 1 | L/HA | ERU | 73.0 c | 0.605 c | 1049 c | 1200 b | 2.25 b | 2.37 a | 24.91 c |
| 4 | PULSE | .2 | % V/V | ERU | | | | | | | |
| 5 | OTHER | | | HOOK | 77.8 b | 0.636 c | 1119 c | 1217 b | 2.34 b | 1.24 b | 13.86 d |
| LSD (P = .05) | | | | | 4.53 | 0.0821 | 111.8 | 117.8 | 0.179 | 0.133 | 3.346 |
| Standard Deviation | | | | | 3.29 | 0.0596 | 81.1 | 85.5 | 0.130 | 0.096 | 2.428 |
| CV | | | | | 4.18 | 8.21 | 6.88 | 7.45 | 5.58 | 4.5 | 9.59 |

EXAMPLE 5

Trial to evaluate sequential applications of 120 mg/ha metsulfuron-methyl (Compound 1), in association with application of 1 L/ha Sunny, in a morphine crop. Sunny and Sunny+metsulfuron-methyl applications were made at 12-14 leaf stage. Metsulfuron-methyl was further applied, with crop at early run-up and bud-emergence. Plant heights and percent lodging were measured 12 days later and the day of capsule harvest respectively.

TABLE 5

| Trt No. | Trt Name | Rate | Rate Unit | Grow Stg | HEIGHT cm | LODGING % | CAPS/ SEED RATIO | STRAW kg/ha | SEED kg/ha | CROP WEIGHT t/ha | STRAW MORPHINE % | MOR-PHINE-kg/ha |
|---|---|---|---|---|---|---|---|---|---|---|---|---|
| 1 | NIL | | | | 107.0 a | 19.0 b | 0.503 c | 1736 c | 2406 a | 4.14 a | 1.43 b | 24.89 c |
| 2 | SUNNY | 1 | L/HA | 12-14L | 86.6 b | 38.0 a | 0.516 c | 1619 c | 2182 a | 3.80 a | 1.63 a | 26.35 bc |
| 2 | PULSE | .2 | % V/V | 12-14L | | | | | | | | |
| 3 | SUNNY | 1 | L/HA | 12-14L | 87.6 b | 35.0 a | 0.590 c | 1775 c | 2094 a | 3.87 a | 1.71 a | 30.50 b |
| 3 | COMPOUND 1 | 120 | MG/HA | 12-14L | | | | | | | | |
| 3 | PULSE | .2 | % V/V | 12-14L | | | | | | | | |

TABLE 5-continued

| Rating Unit | | | | HEIGHT cm | LODGING % | CAPS/ SEED RATIO | STRAW kg/ha | SEED kg/ha | CROP WEIGHT t/ha | STRAW MORPHINE % | MOR- PHINE- kg/ha |
|---|---|---|---|---|---|---|---|---|---|---|---|
| Trt No. | Trt Name | Rate | Rate Unit | Grow Stg | | | | | | | |
| 4 | SUNNY | 1 | L/HA | 12-14L | 84.8 b | 5.0 c | 2.193 b | 2413 b | 791 b | 3.20 b | 1.73 a | 41.77 a |
| 4 | COMPOUND 1 | 120 | MG/HA | 12-14L | | | | | | | | |
| 4 | PULSE | .2 | % V/V | 12-14L | | | | | | | | |
| 4 | COMPOUND 1 | 120 | MG/HA | ERU | | | | | | | | |
| 4 | PULSE | .2 | % V/V | ERU | | | | | | | | |
| 5 | SUNNY | 1 | L/HA | 12-14L | 74.8 c | 2.8 c | 6.455 a | 2697 a | 306 c | 3.00 b | 1.59 a | 42.93 a |
| 5 | COMPOUND 1 | 120 | MG/HA | 12-14L | | | | | | | | |
| 5 | PULSE | .2 | % V/V | 12-14L | | | | | | | | |
| 5 | COMPOUND 1 | 120 | MG/HA | ERU | | | | | | | | |
| 5 | PULSE | .2 | % V/V | ERU | | | | | | | | |
| 5 | COMPOUND 1 | 120 | MG/HA | BE | | | | | | | | |
| 5 | PULSE | .2 | % V/V | BE | | | | | | | | |
| LSD (P = .05) | | | | | 3.00 | 12.05 | 0.9992 | 186.5 | 312.6 | 0.398 | 0.136 | 4.884 |
| Standard Dev | | | | | 2.18 | 8.75 | 0.7251 | 135.3 | 226.8 | 0.289 | 0.099 | 3.544 |
| CV | | | | | 2.47 | 43.82 | 35.34 | 6.61 | 14.58 | 8.01 | 6.09 | 10.65 |

EXAMPLE 6

Trial to evaluate one or two applications of 120 mg/ha metsulfuron-methyl (Compound 1) after 1 L/ha Sunny, and compare with two applications of metsulfuron-methyl alone. Sunny was applied with crop at 12-14 leaf, metsulfuron-methyl to crop at 12-14 leaf, early run-up and bud-emergence stages. Plant heights were measured at early-full flower and percent lodging was measured on the day of capsule harvest.

TABLE 6

| Rating Unit | | | | PLANT HEIGHT cm | LODGING % | CAPSULE/ SEED RATIO | STRAW kg/ha | SEED kg/ha | CROP WEIGHT t/ha | STRAW MORPHINE % | MOR- PHINE kg/ha |
|---|---|---|---|---|---|---|---|---|---|---|---|
| Trt No. | Trt Name | Rate | | Grow Stg | | | | | | | |
| 1 | NIL | | | | 96.0 a | 6.4 ab | 0.626 b | 1522 c | 1680 a | 3.20 a | 1.95 ab | 29.7 c |
| 2 | SUNNY | 1 | L/HA | 12-14L | 90.6 b | 7.6 a | 0.586 b | 1525 c | 1807 a | 3.33 a | 2.05 a | 31.4 c |
| 2 | PULSE | .2 | % V/V | 12-14L | | | | | | | | |
| 3 | SUNNY | 1 | L/HA | 12-14L | 89.8 b | 3.0 ab | 1.552 b | 1949 b | 918 b | 2.87 b | 1.89 ab | 36.5 b |
| 3 | PULSE | .2 | % V/V | 12-14L | | | | | | | | |
| 3 | COMPOUND 1 | 120 | MG/HA | ERU | | | | | | | | |
| 3 | PULSE | .2 | % V/V | ERU | | | | | | | | |
| 4 | SUNNY | 1 | L/HA | 12-14L | 84.4 c | 1.2 b | 6.059 a | 2353 a | 284 c | 2.64 bc | 1.81 b | 42.7 a |
| 4 | PULSE | .2 | % V/V | 12-14L | | | | | | | | |
| 4 | COMPOUND 1 | 120 | MG/HA | ERU | | | | | | | | |
| 4 | PULSE | .2 | % V/V | ERU | | | | | | | | |
| 4 | COMPOUND 1 | 120 | MG/HA | BE | | | | | | | | |
| 4 | PULSE | .2 | % V/V | BE | | | | | | | | |
| 5 | COMPOUND 1 | 120 | MG/HA | ERU | 77.4 d | 1.0 b | 6.140 a | 2194 a | 269 c | 2.46 c | 1.77 b | 38.8 b |
| 5 | PULSE | .2 | % V/V | ERU | | | | | | | | |
| 5 | COMPOUND 1 | 120 | MG/HA | BE | | | | | | | | |
| 5 | PULSE | .2 | % V/V | BE | | | | | | | | |
| LSD (P = .05) | | | | | 4.71 | 5.63 | 1.8928 | 233.2 | 236.0 | 0.310 | 0.214 | 3.591 |
| Standard Dev | | | | | 3.42 | 4.09 | 1.3735 | 169.2 | 171.2 | 0.225 | 0.155 | 2.606 |
| CV | | | | | 3.9 | 106.44 | 45.9 | 8.86 | 17.27 | 7.75 | 8.19 | 7.28 |

EXAMPLE 7

Trial to evaluate sequential applications of 120 mg/ha metsulfuron-methyl (Compound 1), in association with application of 1 L/ha Sunny, in a morphine crop. Plant heights were measured at flowering and percent lodging measured on the day of capsule harvest.

TABLE 7

| Trt No. | Trt Name | Rate | Rate Unit | Grow Stg | HEIGHT cm | LODGING % | CAPS/SEED RATIO | STRAW kg/ha | SEED kg/ha | CROP WEIGHT t/ha | STRAW MORPHINE % | MORPHINE kg/ha |
|---|---|---|---|---|---|---|---|---|---|---|---|---|
| 1 | NIL | | | | 100.6 a | 10.6 a | 0.603 c | 1804 bc | 2083 a | 3.89 a | 1.82 b | 33.0 b |
| 2 | SUNNY | 1 | L/HA | 12-14L | 77.6 b | 7.6 b | 0.684 cd | 1637 c | 1805 ab | 3.44 ab | 2.02 a | 33.0 b |
| 2 | PULSE | .2 | % V/V | 12-14L | | | | | | | | |
| 3 | SUNNY | 1 | L/HA | 12-14L | 74.0 bc | 4.0 c | 1.006 c | 2024 b | 1444 b | 3.47 ab | 2.02 a | 40.9 b |
| 3 | PULSE | .2 | % V/V | 12-14L | | | | | | | | |
| 3 | COMPND 1 | 120 | MG/HA | ERU | | | | | | | | |
| 3 | PULSE | .2 | % V/V | ERU | | | | | | | | |
| 4 | SUNNY | 1 | L/HA | 12-14L | 70.6 c | 1.6 c | 2.440 b | 2401 a | 685 c | 3.09 b | 2.06 a | 49.6 a |
| 4 | PULSE | .2 | % V/V | 12-14L | | | | | | | | |
| 4 | COMPND 1 | 120 | MG/HA | ERU | | | | | | | | |
| 4 | PULSE | .2 | % V/V | ERU | | | | | | | | |
| 4 | COMPND 1 | 120 | MG/HA | MRU | | | | | | | | |
| 4 | PULSE | .2 | % V/V | MRU | | | | | | | | |
| 5 | SUNNY | .5 | L/HA | 12-14L | 77.8 b | 1.8 c | 3.046 a | 2413 a | 553 c | 2.96 b | 2.00 a | 48.7 a |
| 5 | PULSE | .2 | % V/V | 12-14L | | | | | | | | |
| 5 | SUNNY | .5 | L/HA | ERU | | | | | | | | |
| 5 | COMPND 1 | 120 | MG/HA | ERU | | | | | | | | |
| 5 | PULSE | .2 | % V/V | ERU | | | | | | | | |
| 5 | COMPND 1 | 120 | MG/HA | MRU | | | | | | | | |
| 5 | PULSE | .2 | % V/V | MRU | | | | | | | | |
| LSD (P = .05) | | | | | 3.99 | 2.84 | 0.3381 | 331.6 | 403.5 | 0.497 | 0.139 | 7.681 |
| Standard De | | | | | 2.90 | 2.06 | 0.2453 | 240.6 | 292.8 | 0.360 | 0.101 | 5.573 |
| CV | | | | | 3.62 | 40.31 | 15.77 | 11.7 | 22.28 | 10.7 | 5.07 | 13.58 |

EXAMPLE 8

Trial to evaluate metsulfuron-methyl (Compound 1) with Moddus (trinexapac-ethyl) in Lontrel (clopyralid)-treated thebaine crop. Lontrel (1 L/ha, all plots), Moddus, and Moddus/metsulfuron-methyl were applied to crop at 12-14 leaf, late run-up/early bud-emergence and early hook stages, respectively.

TABLE 8

| Trt No. | Treatment Name | Rate | Rate Unit | Growth Stage | HEIGHT cm | CAPS/SEED RATIO | STRAW kg/ha | SEED kg/ha | CROP WEIGHT kg/ha | STRAW THEBAINE % | THEBAINE kg/ha |
|---|---|---|---|---|---|---|---|---|---|---|---|
| 1 | NIL | | | | 124.2 a | 0.954 b | 1579 a | 1201 a | 2.78 a | 0.99 a | 15.7 a |
| 2 | MODDUS | 1 | L/HA | LRU/BE | 126.6 a | 1.467 b | 1686 a | 798 ab | 2.48 a | 1.70 a | 28.6 a |
| 3 | MODDUS | 1 | L/HA | LRU/BE | 110.2 b | 5.408 a | 1588 a | 217 b | 1.81 a | 1.83 a | 29.1 a |
| 3 | COMPOUND 1 | 120 | MG/HA | E HOOK | | | | | | | |
| 3 | PULSE | .2 | % V/V | E HOOK | | | | | | | |
| 4 | OTHER | 1 | L/HA | LRU/BE | 125.0 a | 1.679 b | 1616 a | 713 ab | 2.33 a | 1.72 a | 27.8 a |
| 5 | OTHER | 1 | L/HA | LRU/BE | 126.0 a | 1.617 b | 1582 a | 708 ab | 2.29 a | 1.80 a | 28.5 a |
| LSD (P = .05) | | | | | 4.81 | 2.6874 | 1860.9 | 873.2 | 2.714 | 1.8534 | 29.857 |
| Standard Deviation | | | | | 3.49 | 1.6481 | 1141.3 | 535.5 | 1.665 | 1.1366 | 18.311 |
| CV | | | | | 2.85 | 74.08 | 70.89 | 73.62 | 71.22 | 70.66 | 70.6 |

EXAMPLE 9

Trial to evaluate applications of mesosulfuron-methyl (Compound 2) and metsulfuron-methyl (Compound 1), in a morphine crop. Treatment sprays were applied to crop at ground cover, late run-up and early bud-emergence, respectively. Plant heights were measured at green capsule stage, and lodging assessed on the day of capsule harvest.

TABLE 9

| Trt No. | Treatment Name | Rate | Rate Unit | Grow Stg | HEIGHT cm | LODGING % | CAPSULE/ SEED RATIO | STRAW kg/ha | SEED kg/ha | CROP WEIGHT t/ha | STRAW MORPHINE % | MORPHINE kg/ha |
|---|---|---|---|---|---|---|---|---|---|---|---|---|
| 1 | NIL | | | | 101.3 a | 13.5 a | 0.540 b | 1592 b | 2043 a | 3.63 a | 2.07 a | 28.40 b |
| 2 | COMPOUND 1 | 120 | MG/HA | GC | 94.5 ab | 2.3 c | 3.844 a | 2206 a | 468 b | 2.67 b | 2.04 a | 43.94 a |
| 2 | PULSE | .2 | % V/V | GC | | | | | | | | |
| 2 | COMPOUND 1 | 120 | MG/HA | LRU | | | | | | | | |
| 2 | PULSE | .2 | % V/V | LRU | | | | | | | | |
| 2 | COMPOUND 1 | 120 | MG/HA | EBE | | | | | | | | |
| 2 | PULSE | .2 | % V/V | EBE | | | | | | | | |
| 3 | COMPOUND 2 | 390 | MG/HA | GC | 96.0 ab | 6.5 bc | 2.084 b | 1342 c | 460 b | 1.80 c | 2.10 a | 26.41 b |
| 3 | ACTIVATOR | .125 | % V/V | GC | | | | | | | | |
| 3 | COMPOUND 2 | 390 | MG/HA | EBE | | | | | | | | |
| 3 | ACTIVATOR | .125 | % V/V | EBE | | | | | | | | |
| 4 | COMPOUND 2 | 390 | MG/HA | GC | 89.3 b | 11.0 ab | 1.854 b | 827 d | 336 b | 1.16 d | 2.03 a | 15.27 c |
| 4 | ACTIVATOR | .125 | % V/V | GC | | | | | | | | |
| 4 | COMPOUND 2 | 390 | MG/HA | LRU | | | | | | | | |
| 4 | ACTIVATOR | .125 | % V/V | LRU | | | | | | | | |
| 4 | COMPOUND 2 | 390 | MG/HA | EBE | | | | | | | | |
| 4 | ACTIVATOR | .125 | % V/V | EBE | | | | | | | | |
| LSD (P = .05) | | | | | 7.83 | 4.86 | 1.7235 | 199.5 | 231.2 | 0.378 | 0.127 | 4.748 |
| Standard Deviation | | | | | 4.53 | 2.81 | 0.9961 | 115.3 | 133.6 | 0.218 | 0.073 | 2.744 |
| CV | | | | | 4.75 | 33.8 | 47.88 | 7.73 | 16.17 | 9.42 | 3.56 | 9.63 |

EXAMPLE 10

Trial to evaluate applications of triasulfuron (Compound 3) (525 mg/ha) and metsulfuron-methyl (Compound 1), in a morphine crop. Treatment sprays were applied to crop at ground cover, mid run-up and bud-emergence, respectively.

TABLE 10

| | Rating Unit | | | | | CAPSULE/ | | | CROP | STRAW | |
|---|---|---|---|---|---|---|---|---|---|---|---|
| Trt No. | Treatment Name | Rate | Rate Unit | Grow Stg | HEIGHT cm | SEED RATIO | STRAW kg/ha | SEED kg/ha | WEIGHT t/ha | MORPHINE % | MORPHINE kg/ha |
| 1 | NIL | | | | 97.2 a | 0.674 e | 774 c | 838 a | 1.61 b | 2.28 a | 17.66 c |
| 2 | COMPOUND 1 | 120 | MG/HA | GC | 84.2 b | 11.957 a | 1757 a | 105 c | 1.86 a | 2.25 a | 39.63 a |
| 2 | PULSE | .2 | % V/V | GC | | | | | | | |
| 2 | COMPOUND 1 | 120 | MG/HA | RU | | | | | | | |
| 2 | PULSE | .2 | % V/V | RU | | | | | | | |
| 2 | COMPOUND 1 | 120 | MG/HA | BE | | | | | | | |
| 2 | PULSE | .2 | % V/V | BE | | | | | | | |
| 3 | COMPOUND 3 | 525 | MG/HA | GC | 75.6 c | 1.762 c | 992 b | 408 b | 1.40 c | 2.06 b | 20.55 b |
| 3 | PULSE | .2 | % V/V | GC | | | | | | | |
| 4 | COMPOUND 3 | 525 | MG/HA | GC | 55.0 e | 1.338 d | 113 e | 60 c | 0.17 e | 1.76 c | 1.99 e |
| 4 | PULSE | .2 | % V/V | GC | | | | | | | |
| 4 | COMPOUND 3 | 525 | MG/HA | RU | | | | | | | |
| 4 | PULSE | .2 | % V/V | RU | | | | | | | |
| 5 | COMPOUND 3 | 263 | MG/HA | GC | 71.0 d | 3.170 b | 644 d | 141 c | 0.79 d | 2.03 b | 13.17 d |
| 5 | PULSE | .2 | % V/V | GC | | | | | | | |
| 5 | COMPOUND 3 | 263 | MG/HA | RU | | | | | | | |
| 5 | PULSE | .2 | % V/V | RU | | | | | | | |
| LSD (P = .05) | | | | | 1.83 | 0.0000 | 0.0 | 208.4 | 0.000 | 0.088 | 0.000 |
| Standard Deviation | | | | | 1.33 | 0.0000 | 0.0 | 151.2 | 0.000 | 0.064 | 0.000 |
| CV | | | | | 1.74 | 0.0 | 0.0 | 35.6 | 0.0 | 3.08 | 0.00 |

EXAMPLE 11

Trial to evaluate applications of metsulfuron-methyl (Compound 1), Sunny and metsulfuron-methyl+Sunny, in a morphine crop. Treatment sprays were applied to crop at row cover, early run-up and bud-emergence/early hook. Plant heights were measured at green capsule stage.

TABLE 11

| Trt No. | Treatment Name | Rate | Rate Unit | Grow Stg | HEIGHT cm | LODGING % | CAPSULE/ SEED RATIO | STRAW kg/ha | SEED kg/ha | CROP WEIGHT t/ha | STRAW MORPHINE % | MORPHINE- kg/ha |
|---|---|---|---|---|---|---|---|---|---|---|---|---|
| 1 | NIL | | | | 101.6 a | 4.8 a | 0.573 b | 1805 b | 2182 a | 3.99 a | 1.95 a | 35.16 b |
| 2 | SUNNY | 1 | L/HA | RC | 78.0 b | 3.4 ab | 0.622 b | 1745 bc | 1944 b | 3.69 b | 2.01 a | 35.10 b |
| 2 | SPRAYTECH OIL | 1 | L/HA | RC | | | | | | | | |
| 3 | SUNNY | 1 | L/HA | RC | 80.0 b | 4.1 a | 0.599 b | 1615 c | 1873 b | 3.49 c | 2.00 a | 32.31 b |
| 3 | COMPOUND 1 | 120 | MG/HA | RC | | | | | | | | |
| 3 | SPRAYTECH OIL | 1 | L/HA | RC | | | | | | | | |
| 3 | COMPOUND 1 | 120 | MG/HA | ERU | | | | | | | | |
| 3 | PULSE | .2 | % V/V | ERU | | | | | | | | |
| 4 | COMPOUND 1 | 120 | MG/HA | RC | 99.2 a | 1.2 b | 8.488 a | 2955 a | 267 c | 3.22 d | 2.04 a | 60.39 a |
| 4 | PULSE | .2 | % V/V | RC | | | | | | | | |
| 4 | COMPOUND 1 | 120 | MG/HA | ERU | | | | | | | | |
| 4 | PULSE | .2 | % V/V | ERU | | | | | | | | |
| 4 | COMPOUND 1 | 120 | MG/HA | BE/EH | | | | | | | | |
| 4 | PULSE | .2 | % V/V | BE/EH | | | | | | | | |
| LSD (P = .05) | | | | | 8.10 | 2.26 | 1.7936 | 159.4 | 125.7 | 0.128 | 0.118 | 5.263 |
| Standard Deviation | | | | | 5.88 | 1.64 | 1.3015 | 115.7 | 91.2 | 0.093 | 0.085 | 3.819 |
| CV | | | | | 6.69 | 46.62 | 59.81 | 5.94 | 5.6 | 2.59 | 4.27 | 9.78 |

EXAMPLE 12

Trial to evaluate applications of metsulfuron-methyl (Compound 1), Sunny and metsulfuron-methyl+Sunny, in a morphine crop. Treatment sprays were applied to crop at row cover, early run-up and late run-up. Plant heights were measured at end of flowering.

TABLE 12

| Trt No. | Treatment Name | Rate | Rate Unit | Grow Stg | HEIGHT cm | CAPS/ SEED RATIO | STRAW kg/ha | SEED kg/ha | CROP WEIGHT t/ha | STRAW MORPHINE % | MORPHINE kg/ha |
|---|---|---|---|---|---|---|---|---|---|---|---|
| 1 | NIL | | | | 101.6 a | 0.706 c | 1584 b | 1567 b | 3.15 a | 2.43 b | 38.52 c |
| 2 | SUNNY | .5 | L/HA | RC | 89.0 b | 0.552 c | 1402 b | 1761 a | 3.16 a | 2.54 a | 35.54 c |
| 2 | PULSE | .2 | % V/V | RC | | | | | | | |
| 2 | SUNNY | .5 | L/HA | ERU | | | | | | | |
| 2 | PULSE | .2 | % V/V | LRU | | | | | | | |
| 3 | COMPOUND 1 | 120 | MG/HA | RC | 83.4 bc | 10.444 a | 2099 a | 143 c | 2.24 b | 2.24 c | 47.11 b |
| 3 | PULSE | .2 | % V/V | RC | | | | | | | |
| 3 | COMPOUND 1 | 120 | MG/HA | ERU | | | | | | | |
| 3 | PULSE | .2 | % V/V | ERU | | | | | | | |
| 3 | COMPOUND 1 | 120 | MG/HA | LRU | | | | | | | |
| 3 | PULSE | .2 | % V/V | LRU | | | | | | | |
| 4 | SUNNY | .5 | L/HA | RC | 82.0 c | 8.895 b | 2218 a | 173 c | 2.39 b | 2.55 a | 56.50 a |
| 4 | COMPOUND 1 | 120 | MG/HA | RC | | | | | | | |
| 4 | PULSE | .2 | % V/V | RC | | | | | | | |
| 4 | SUNNY | .5 | L/HA | ERU | | | | | | | |
| 4 | COMPOUND 1 | 120 | MG/HA | ERU | | | | | | | |
| 4 | PULSE | .2 | % V/V | ERU | | | | | | | |
| 4 | COMPOUND 1 | 120 | MG/HA | LRU | | | | | | | |
| 4 | PULSE | .2 | % V/V | LRU | | | | | | | |
| 5 | SUNNY | .5 | L/HA | RC | 83.4 bc | 8.170 b | 2217 a | 190 c | 2.41 b | 2.24 c | 49.55 b |
| 5 | COMPOUND 1 | 120 | MG/HA | RC | | | | | | | |
| 5 | PROVIDE | .25 | L/HA | RC | | | | | | | |
| 5 | PULSE | .2 | % V/V | RC | | | | | | | |
| 5 | SUNNY | .5 | L/HA | ERU | | | | | | | |
| 5 | COMPOUND 1 | 120 | MG/HA | ERU | | | | | | | |
| 5 | PROVIDE | .25 | L/HA | ERU | | | | | | | |
| 5 | PULSE | .2 | % V/V | ERU | | | | | | | |
| 5 | COMPOUND 1 | 120 | MG/HA | LRU | | | | | | | |
| 5 | PULSE | .2 | % V/V | LRU | | | | | | | |
| LSD (P = .05) | | | | | 5.49 | 1.4995 | 234.7 | 130.9 | 0.213 | 0.107 | 5.359 |
| Standard Deviation | | | | | 3.98 | 1.0881 | 170.3 | 95.0 | 0.154 | 0.077 | 3.889 |
| CV | | | | | 4.53 | 18.91 | 8.95 | 12.39 | 5.78 | 3.22 | 8.56 |

EXAMPLE 13

Trial to evaluate applications of metsulfuron-methyl (Compound 1), Lontrel and metsulfuron-methyl+Lontrel, in a morphine crop. Treatment sprays were applied to crop at row cover, early run-up and late run-up. Plant heights were measured at green capsule stage. Lodging was assessed at harvest.

TABLE 13

| Trt No. | Treatment Name | Rate | Rate Unit | Grow Stg | HEIGHT cm | LODGING % | CAPS/ SEED RATIO | STRAW kg/ha | SEED kg/ha | CROP WEIGHT t/ha | STRAW MORPHINE % | MOR- PHINE kg/ha |
|---|---|---|---|---|---|---|---|---|---|---|---|---|
| 1 | NIL | | | | 99.6 ab | 9.6 a | 0.714 b | 1829 c | 1863 a | 3.69 a | 1.87 b | 34.15 b |
| 2 | LONTREL | 1 | L/HA | RC | 104.8 a | 4.0 b | 1.074 b | 2138 b | 1422 b | 3.56 a | 2.12 a | 45.50 a |
| 3 | COMPOUND 1 | 120 | MG/HA | RC | 95.8 b | 2.2 b | 3.431 a | 2530 a | 582 c | 3.11 b | 2.01 a | 50.81 a |
| 3 | PULSE | .2 | % V/V | RC | | | | | | | | |
| 3 | COMPOUND 1 | 120 | MG/HA | ERU | | | | | | | | |
| 3 | PULSE | .2 | % V/V | ERU | | | | | | | | |
| 3 | COMPOUND 1 | 120 | MG/HA | LRU | | | | | | | | |
| 3 | PULSE | .2 | % V/V | LRU | | | | | | | | |
| 4 | LONTREL | 1 | L/HA | RC | 105.2 a | 2.2 b | 2.612 a | 2473 a | 725 c | 3.20 b | 2.08 a | 51.58 a |
| 4 | COMPOUND 1 | 120 | MG/HA | RC | | | | | | | | |
| 4 | PULSE | .2 | % V/V | RC | | | | | | | | |
| 4 | COMPOUND 1 | 120 | MG/HA | ERU | | | | | | | | |
| 4 | PULSE | .2 | % V/V | ERU | | | | | | | | |
| 4 | COMPOUND 1 | 120 | MG/HA | LRU | | | | | | | | |
| 4 | PULSE | .2 | % V/V | LRU | | | | | | | | |
| 5 | LONTREL | 1 | L/HA | RC | 101.4 ab | 2.4 b | 2.658 a | 2379 a | 697 c | 3.08 b | 2.05 a | 48.75 a |
| 5 | COMPOUND 1 | 120 | MG/HA | RC | | | | | | | | |
| 5 | PROVIDE | .25 | L/HA | RC | | | | | | | | |
| 5 | PULSE | .2 | % V/V | RC | | | | | | | | |
| 5 | COMPOUND 1 | 120 | MG/HA | ERU | | | | | | | | |
| 5 | PULSE | .2 | % V/V | ERU | | | | | | | | |
| 5 | PROVIDE | .25 | L/HA | ERU | | | | | | | | |
| 5 | COMPOUND 1 | 120 | MG/HA | LRU | | | | | | | | |
| 5 | PULSE | .2 | % V/V | LRU | | | | | | | | |
| LSD (P = .05) | | | | | 7.57 | 3.36 | 1.1127 | 185.5 | 346.5 | 0.355 | 0.130 | 5.729 |
| Standard Deviation | | | | | 5.49 | 2.44 | 0.8074 | 134.6 | 251.4 | 0.258 | 0.094 | 4.157 |
| CV | | | | | 5.42 | 59.84 | 38.49 | 5.93 | 23.77 | 7.74 | 4.66 | 9.01 |

EXAMPLE 14

Trial to evaluate combinations of metsulfuron-methyl (Compound 1), Lontrel and Moddus, in a thebaine crop. Treatment sprays were applied to crop at ground cover, mid-late run-up and late bud-emergence/early hook, respectively. Plant heights and general appearance (1-3 scale, where 1=healthy crop and 3=sickly-looking crop) were assessed at early green capsule stage.

TABLE 14

| Trt No. | Treatment Name | Rate | Rate Unit | Grow Stg | HEIGHT cm | APPEAR- ANCE 1-3 | CAPS/ SEED RATIO | STRAW kg/ha | SEED kg/ha | CROP WEIGHT t/ha | STRAW THEBAINE % | THEBA- INE kg/ha |
|---|---|---|---|---|---|---|---|---|---|---|---|---|
| 1 | LONTREL | .8 | L/HA | GC | 103.8 a | 1.0 d | 32.043 a | 1061 a | 27 c | 1.09 a | 2.24 b | 23.73 a |
| 1 | MODDUS | .5 | L/HA | GC | | | | | | | | |
| 1 | MODDUS | .5 | L/HA | M-LRU | | | | | | | | |
| 2 | MODDUS | .5 | L/HA | GC | 90.4 b | 1.4 cd | 5.636 c | 927 a | 122 a | 1.05 a | 2.24 b | 20.77 a |
| 2 | COMPOUND 1 | 120 | MG/HA | GC | | | | | | | | |
| 2 | PULSE | .2 | % V/V | GC | | | | | | | | |
| 2 | MODDUS | .5 | L/HA | M-LRU | | | | | | | | |
| 2 | COMPOUND 1 | 120 | MG/HA | M-LRU | | | | | | | | |
| 2 | PULSE | .2 | % V/V | M-LRU | | | | | | | | |
| 3 | LONTREL | .8 | L/HA | GC | 77.0 c | 2.1 ab | 20.936 b | 566 c | 19 c | 0.58 c | 2.36 c | 13.39 b |
| 3 | MODDUS | .5 | L/HA | GC | | | | | | | | |
| 3 | COMPOUND 1 | 120 | MG/HA | GC | | | | | | | | |
| 3 | PULSE | .2 | % V/V | GC | | | | | | | | |
| 3 | MODDUS | .5 | L/HA | M-LRU | | | | | | | | |
| 3 | COMPOUND 1 | 120 | MG/HA | M-LRU | | | | | | | | |

TABLE 14-continued

| Trt No. | Treatment Name | Rate | Rate Unit | Grow Stg | HEIGHT cm | APPEARANCE 1-3 | CAPS/SEED RATIO | STRAW kg/ha | SEED kg/ha | CROP WEIGHT t/ha | STRAW THEBAINE % | THEBAINE kg/ha |
|---|---|---|---|---|---|---|---|---|---|---|---|---|
| 3 | PULSE | .2 | % V/V | M-LRU | | | | | | | | |
| 4 | LONTREL | .5 | L/HA | GC | 74.6 c | 2.2 a | 12.964 c | 515 c | 29 c | 0.54 c | 2.41 a | 12.40 b |
| 4 | MODDUS | .5 | L/HA | GC | | | | | | | | |
| 4 | COMPOUND 1 | 120 | MG/HA | GC | | | | | | | | |
| 4 | PULSE | .2 | % V/V | GC | | | | | | | | |
| 4 | MODDUS | .5 | L/HA | M-LRU | | | | | | | | |
| 4 | COMPOUND 1 | 120 | MG/HA | M-LRU | | | | | | | | |
| 4 | PULSE | .2 | % V/V | M-LRU | | | | | | | | |
| 5 | MODDUS | .5 | L/HA | GC | 76.4 c | 1.7 bc | 8.261 c | 761 b | 65 b | 0.83 b | 2.03 c | 15.48 b |
| 5 | COMPOUND 1 | 120 | MG/HA | GC | | | | | | | | |
| 5 | PULSE | .2 | % V/V | GC | | | | | | | | |
| 5 | MODDUS | .5 | L/HA | M-LRU | | | | | | | | |
| 5 | COMPOUND 1 | 120 | MG/HA | M-LRU | | | | | | | | |
| 5 | PULSE | .2 | % V/V | M-LRU | | | | | | | | |
| 5 | COMPOUND 1 | 120 | MG/HA | LBE/EH | | | | | | | | |
| 5 | PULSE | .2 | % V/V | LBE/EH | | | | | | | | |
| LSD (P = .05) | | | | | 7.07 | 0.46 | 7.8996 | 141.8 | 22.1 | 0.146 | 0.084 | 3.376 |
| Standard Deviation | | | | | 5.13 | 0.33 | 5.7321 | 102.9 | 16.0 | 0.106 | 0.061 | 2.450 |
| CV | | | | | 6.08 | 19.74 | 35.9 | 13.44 | 30.68 | 12.96 | 2.7 | 14.28 |

EXAMPLE 15

Trial to evaluate combinations of metsulfuron-methyl (Compound 1), Lontrel and Moddus, in a thebaine crop. Treatment sprays were applied to crop at late row cover, late run-up and early hook stages, respectively. Plant heights and crop appearance (1-3 scale) were assessed at green capsule stage.

EXAMPLE 16

Trial to evaluate applications of metsulfuron-methyl (Compound 1), mesosulfuron-methyl (Compound 2) and triasulfuron (Compound 3), in a morphine crop. Treatment sprays were applied to crop at row cover and ground cover/early run-up, respectively. Plant heights were assessed 5 weeks after last application and lodging was assessed at capsule harvest. Lodging was assessed as negligible.

TABLE 15

| Trt No. | Treatment Name | Rate | Rate Unit | Grow Stg | HEIGHT cm | APPEARANCE 1-3 | CAPS/SEED RATIO | STRAW kg/ha | SEED kg/ha | CROP WEIGHT t/ha | STRAW THEBAINE % | THEBAINE kg/ha |
|---|---|---|---|---|---|---|---|---|---|---|---|---|
| 1 | LONTREL | .8 | L/HA | LRC | 106.6 a | 1.0 b | 7.546 a | 1395 a | 134 b | 1.53 a | 1.81 bc | 25.2 a |
| 1 | MODDUS | .5 | L/HA | LRC | | | | | | | | |
| 1 | MODDUS | .5 | L/HA | LRU | | | | | | | | |
| 2 | MODDUS | .5 | L/HA | LRC | 75.2 b | 1.1 b | 3.862 c | 1308 a | 291 a | 1.60 a | 1.91 ab | 25.2 a |
| 2 | COMPOUND 1 | 120 | MG/HA | LRC | | | | | | | | |
| 2 | PULSE | .2 | % V/V | LRC | | | | | | | | |
| 2 | MODDUS | .5 | L/HA | LRU | | | | | | | | |
| 2 | COMPOUND 1 | 120 | MG/HA | LRU | | | | | | | | |
| 2 | PULSE | .2 | % V/V | LRU | | | | | | | | |
| 3 | LONTREL | .5 | L/HA | LRC | 74.6 b | 1.5 a | 3.988 c | 975 b | 183 b | 1.16 b | 1.97 a | 19.3 b |
| 3 | MODDUS | .5 | L/HA | LRC | | | | | | | | |
| 3 | COMPOUND 1 | 120 | MG/HA | LRC | | | | | | | | |
| 3 | PULSE | .2 | % V/V | LRC | | | | | | | | |
| 3 | MODDUS | .5 | L/HA | LRU | | | | | | | | |
| 3 | COMPOUND 1 | 120 | MG/HA | LRU | | | | | | | | |
| 3 | PULSE | .2 | % V/V | LRU | | | | | | | | |
| 4 | LONTREL | .5 | L/HA | LRC | 59.0 d | 1.8 a | 5.653 bc | 764 bc | 95 b | 0.86 c | 1.78 c | 13.6 c |
| 4 | MODDUS | .5 | L/HA | LRC | | | | | | | | |
| 4 | COMPOUND 1 | 120 | MG/HA | LRC | | | | | | | | |
| 4 | PULSE | .2 | % V/V | LRC | | | | | | | | |
| 4 | MODDUS | .5 | L/HA | LRU | | | | | | | | |
| 4 | COMPOUND 1 | 120 | MG/HA | LRU | | | | | | | | |
| 4 | PULSE | .2 | % V/V | LRU | | | | | | | | |
| 4 | COMPOUND 1 | 120 | MG/HA | EH | | | | | | | | |
| 4 | PULSE | .2 | % V/V | EH | | | | | | | | |
| 5 | MODDUS | .5 | L/HA | LRC | 63.8 c | 1.9 a | 6.648 ab | 698 c | 84 b | 0.78 c | 1.7 c | 12.0 c |
| 5 | COMPOUND 1 | 120 | MG/HA | LRC | | | | | | | | |
| 5 | PULSE | .2 | % V/V | LRC | | | | | | | | |
| 5 | MODDUS | .5 | L/HA | LRU | | | | | | | | |
| 5 | COMPOUND 1 | 120 | MG/HA | LRU | | | | | | | | |
| 5 | PULSE | .2 | % V/V | LRU | | | | | | | | |
| 5 | COMPOUND 1 | 120 | MG/HA | EH | | | | | | | | |
| 5 | PULSE | .2 | % V/V | EH | | | | | | | | |
| LSD (P = .05) | | | | | 4.62 | 0.37 | 1.7416 | 216.9 | 99.3 | 0.242 | 0.107 | 4.402 |
| Standard Deviation | | | | | 3.35 | 0.27 | 1.2637 | 157.4 | 72.0 | 0.176 | 0.078 | 3.194 |
| CV | | | | | 4.42 | 18.28 | 22.81 | 15.32 | 45.72 | 14.82 | 4.25 | 16.76 |

TABLE 16

| Trt No. | Treatment Name | Rate | Rate Unit | Grow Stg | PLANT HEIGHT cm | CAPS/ SEED RATIO | STRAW kg/ha | SEED kg/ha | CROP WEIGHT t/ha | STRAW MORPHINE % | MORPHINE kg/ha |
|---|---|---|---|---|---|---|---|---|---|---|---|
| 1 | NIL | | | | 111.6 a | 0.590 d | 1806 bc | 2155 a | 3.98 a | 2.16 ab | 39.05 bc |
| 2 | COMPOUND 1 | 120 | MG/HA | RC | 90.0 c | 1.740 a | 1749 bc | 698 d | 2.46 c | 2.15 ab | 37.76 bc |
| 2 | PULSE | .2 | % V/V | RC | | | | | | | |
| 2 | COMPOUND 1 | 120 | MG/HA | GC/ERU | | | | | | | |
| 2 | PULSE | .2 | % V/V | GC/ERU | | | | | | | |
| 3 | COMPOUND 3 | 75 | MG/HA | RC | 103.4 b | 1.259 b | 2211 a | 1233 c | 3.47 b | 2.21 a | 49.16 a |
| 3 | PULSE | .2 | % V/V | RC | | | | | | | |
| 3 | COMPOUND 3 | 75 | MG/HA | GC/ERU | | | | | | | |
| 3 | PULSE | .2 | % V/V | GC/ERU | | | | | | | |
| 4 | COMPOUND 3 | 150 | MG/HA | RC | 88.6 c | 1.959 a | 1589 c | 581 d | 2.18 c | 2.03 b | 32.34 c |
| 4 | PULSE | .2 | % V/V | RC | | | | | | | |
| 4 | COMPOUND 3 | 150 | MG/HA | GC/ERU | | | | | | | |
| 4 | PULSE | .2 | % V/V | GC/ERU | | | | | | | |
| 5 | COMPOUND 2 | 150 | MG/HA | RC | 101.6 b | 0.825 c | 1976 ab | 1671 b | 3.65 ab | 2.21 a | 43.77 ab |
| 5 | ACTIVATOR | .125 | % V/V | RC | | | | | | | |
| 5 | COMPOUND 2 | 150 | MG/HA | GC/ERU | | | | | | | |
| 5 | ACTIVATOR | .125 | % V/V | GC/ERU | | | | | | | |
| LSD (P = .05) | | | | | 6.39 | 0.2316 | 266.8 | 170.6 | 0.363 | 0.159 | 7.690 |
| Standard Deviation | | | | | 4.64 | 0.1680 | 193.6 | 123.8 | 0.263 | 0.115 | 5.580 |
| CV | | | | | 4.68 | 13.18 | 10.37 | 9.76 | 8.36 | 5.35 | 13.81 |

EXAMPLE 17

Trial to evaluate applications of triasulfuron, mesosulfuron-methyl and metsulfuron-methyl, in a morphine crop. Treatment sprays were applied to with crop at early run-up and mid-late run-up, respectively. Plant heights were measured on 6 weeks after last application and lodging was assessed at capsule harvest.

TABLE 17

| Trt No. | Treatment Name | Rate | Rate Unit | Grow Stg | PLANT HEIGHT cm | LODG- ING % | CAPS/ SEED RATIO | STRAW kg/ha | SEED kg/ha | CROP WEIGHT t/ha | STRAW MORPHINE % | MORPHINE kg/ha |
|---|---|---|---|---|---|---|---|---|---|---|---|---|
| 1 | NIL | | | | 112.4 a | 2.7 b | 0.927 e | 1861 b | 1434 a | 3.35 a | 2.41 a | 45.08 ab |
| 2 | COMPOUND 1 | 120 | MG/HA | ERU | 97.0 c | 2.7 b | 8.976 a | 2343 a | 187 c | 2.60 b | 2.11 c | 49.48 a |
| 2 | PULSE | .2 | % V/V | ERU | | | | | | | | |
| 2 | COMPOUND 1 | 120 | MG/HA | M-LRU | | | | | | | | |
| 2 | PULSE | .2 | % V/V | M-LRU | | | | | | | | |
| 3 | COMPOUND 3 | 75 | MG/HA | ERU | 100.2 bc | 1.6 b | 3.677 c | 2299 a | 451 b | 2.79 b | 2.26 b | 51.94 a |
| 3 | PULSE | .2 | % V/V | ERU | | | | | | | | |
| 3 | COMPOUND 3 | 75 | MG/HA | M-LRU | | | | | | | | |
| 3 | PULSE | .2 | % V/V | M-LRU | | | | | | | | |
| 4 | COMPOUND 3 | 150 | MG/HA | ERU | 90.4 d | 11.9 a | 6.016 b | 1331 c | 175 c | 1.71 c | 1.93 d | 25.78 c |
| 4 | PULSE | .2 | % V/V | ERU | | | | | | | | |
| 4 | COMPOUND 3 | 150 | MG/HA | M-LRU | | | | | | | | |
| 4 | PULSE | .2 | % V/V | M-LRU | | | | | | | | |
| 5 | COMPOUND 2 | 150 | MG/HA | ERU | 104.0 b | 2.8 b | 2.315 d | 1910 b | 612 b | 2.57 b | 2.23 b | 41.97 b |
| 5 | ACTIVATOR | .125 | % V/V | ERU | | | | | | | | |
| 5 | COMPOUND 2 | 150 | MG/HA | M-LRU | | | | | | | | |
| 5 | ACTIVATOR | .125 | % V/V | M-LRU | | | | | | | | |
| LSD (P = .05) | | | | | 6.07 | 3.79 | 1.0654 | 272.1 | 186.6 | 0.424 | 0.102 | 6.692 |
| Standard Deviation | | | | | 4.40 | 2.65 | 0.7561 | 193.1 | 132.4 | 0.301 | 0.073 | 4.749 |
| CV | | | | | 4.37 | 61.0 | 17.25 | 9.91 | 23.16 | 11.55 | 3.35 | 11.08 |

EXAMPLE 18

Trial to evaluate applications of triasulfuron, mesosulfuron-methyl and metsulfuron-methyl, in a morphine crop. Treatment sprays were applied to crop at row cover, mid run-up and early hook stages, respectively. Plant heights were measured 5 weeks after last application and lodging at capsule harvest.

TABLE 18

| Trt No. | Treatment Name | Rate | Rate Unit | Grow Stg | PLANT HEIGHT cm | LODGING % | CAPS/ SEED RATIO | STRAW kg/ha | SEED kg/ha | CROP WEIGHT t/ha | STRAW MORPHINE % | MOR- PHINE kg/ha |
|---|---|---|---|---|---|---|---|---|---|---|---|---|
| 1 | NIL | | | | 101.4 a | 3.4 a | 0.540 c | 1468 c | 1968 a | 3.49 a | 2.38 a | 35.03 c |
| 2 | COMPOUND 1 | 120 | MG/HA | RC | 88.0 d | 1.8 a | 2.543 a | 2186 a | 643 c | 2.87 b | 2.13 c | 46.52 b |
| 2 | PULSE | .2 | % V/V | RC | | | | | | | | |
| 2 | COMPOUND 1 | 120 | MG/HA | MRU | | | | | | | | |
| 2 | PULSE | .2 | % V/V | MRU | | | | | | | | |
| 2 | COMPOUND 1 | 120 | MG/HA | LRU | | | | | | | | |
| 2 | PULSE | .2 | % V/V | LRU | | | | | | | | |
| 3 | COMPOUND 3 | 75 | MG/HA | RC | 93.0 c | 2.2 a | 1.358 b | 2217 a | 1161 b | 3.43 a | 2.33 a | 51.88 a |
| 3 | PULSE | .2 | % V/V | RC | | | | | | | | |
| 3 | COMPOUND 3 | 75 | MG/HA | MRU | | | | | | | | |
| 3 | PULSE | .2 | % V/V | MRU | | | | | | | | |
| 3 | COMPOUND 3 | 75 | MG/HA | LRU | | | | | | | | |
| 3 | PULSE | .2 | % V/V | LRU | | | | | | | | |
| 4 | COMPOUND 3 | 150 | MG/HA | RC | 81.4 d | 2.6 a | 2.664 a | 1797 b | 482 c | 2.32 c | 2.09 c | 37.62 c |
| 4 | PULSE | .2 | % V/V | RC | | | | | | | | |
| 4 | COMPOUND 3 | 150 | MG/HA | MRU | | | | | | | | |
| 4 | PULSE | .2 | % V/V | MRU | | | | | | | | |
| 4 | COMPOUND 3 | 150 | MG/HA | LRU | | | | | | | | |
| 4 | PULSE | .2 | % V/V | LRU | | | | | | | | |
| 5 | COMPOUND 2 | 150 | MG/HA | RC | 96.4 b | 2.8 a | 1.071 b | 1917 b | 1281 b | 3.25 a | 2.23 b | 42.83 b |
| 5 | ACTIVATOR | .125 | % V/V | RC | | | | | | | | |
| 5 | COMPOUND 2 | 150 | MG/HA | MRU | | | | | | | | |
| 5 | ACTIVATOR | .125 | % V/V | MRU | | | | | | | | |
| 5 | COMPOUND 2 | 150 | MG/HA | LRU | | | | | | | | |
| 5 | ACTIVATOR | .125 | % V/V | LRU | | | | | | | | |
| LSD (P = Various) | | | | | 3.18 | 1.80 | 0.4639 | 175.1 | 235.0 | 0.318 | 0.092 | 4.909 |
| Standard Deviation | | | | | 2.31 | 1.31 | 0.3366 | 127.1 | 170.5 | 0.231 | 0.067 | 3.562 |
| CV | | | | | 2.51 | 51.03 | 20.58 | 6.63 | 15.41 | 7.51 | 3.0 | 8.33 |

EXAMPLE 19

Trial to evaluate applications of sulfosulfuron, thifensulfuron-methyl and metsulfuron-methyl, in a morphine crop. Treatment sprays were applied to crop at mid-late run-up and late-run-up/bud-emergence, respectively. Plant heights were measured some 10 weeks after the last application. Lodging was assessed at capsule harvest.

TABLE 19

| Trt No. | Treatment Name | Rate | Rate Unit | Grow Stg | PLANT HEIGHT cm | CAP- SULE/ SEED RATIO | STRAW kg/ha | SEED kg/ha | CROP WEIGHT t/ha | STRAW MORPHINE % | MOR- PHINE kg/ha |
|---|---|---|---|---|---|---|---|---|---|---|---|
| 1 | NIL | | | | 85 | .638 | 875 | 961 | 1.84 | 2.43 | 21.12 |
| 2 | COMPOUND 1 | 120 | MG/HA | M-LRU | 72 | 6.352 | 1203 | 131 | 1.33 | 1.80 | 21.65 |
| 2 | PULSE | .2 | % V/V | M-LRU | | | | | | | |
| 2 | COMPOUND 1 | 120 | MG/HA | LRU-BE | | | | | | | |
| 2 | PULSE | .2 | % V/V | LRU-BE | | | | | | | |
| 3 | COMPOUND 4 | 450 | MG/HA | M-LRU | 78 | 5.209 | 771 | 103 | 0.87 | 2.10 | 16.19 |
| 3 | ACTIVATOR | .125 | % V/V | M-LRU | | | | | | | |
| 3 | COMPOUND 4 | 450 | MG/HA | LRU-BE | | | | | | | |
| 3 | ACTIVATOR | .125 | % V/V | LRU-BE | | | | | | | |
| 4 | COMPOUND 4 | 1.35 | G/HA | M-LRU | 65 | 3.299 | 184 | 39 | 0.22 | 2.23 | 4.10 |
| 4 | ACTIVATOR | .125 | % V/V | M-LRU | | | | | | | |
| 4 | COMPOUND 4 | 1.35 | G/HA | LRU-BE | | | | | | | |
| 4 | ACTIVATOR | .125 | % V/V | LRU-BE | | | | | | | |
| 5 | COMPOUND 4 | 4.5 | G/HA | M-LRU | 0 | 0 | 0 | 0 | 0 | 0 | 0 |
| 5 | ACTIVATOR | .125 | % V/V | M-LRU | | | | | | | |
| 5 | COMPOUND 4 | 4.5 | G/HA | LRU-BE | | | | | | | |
| 5 | ACTIVATOR | .125 | % V/V | LRU-BE | | | | | | | |
| 6 | COMPOUND 5 | 60 | MG/HA | M-LRU | 73 | 2.324 | 738 | 220 | .96 | 2.6 | 19.19 |
| 6 | SWIFT | 1 | % V/V | M-LRU | | | | | | | |
| 6 | COMPOUND 5 | 60 | MG/HA | LRU-BE | | | | | | | |
| 6 | SWIFT | 1 | % V/V | LRU-BE | | | | | | | |
| 7 | COMPOUND 5 | 180 | MG/HA | M-LRU | 75 | 2.898 | 931 | 223 | 1.15 | 2.46 | 22.90 |
| 7 | SWIFT | 1 | % V/V | M-LRU | | | | | | | |
| 7 | COMPOUND 5 | 180 | MG/HA | LRU-BE | | | | | | | |

TABLE 19-continued

| Trt No. | Treatment Name | Rate | Rate Unit | Grow Stg | PLANT HEIGHT cm | CAPSULE/ SEED RATIO | STRAW kg/ha | SEED kg/ha | CROP WEIGHT t/ha | STRAW MORPHINE % | MORPHINE kg/ha |
|---|---|---|---|---|---|---|---|---|---|---|---|
| 7 | SWIFT | 1 | % V/V | LRU-BE | | | | | | | |
| 8 | COMPOUND 5 | 600 | MG/HA | M-LRU | 80 | 4.564 | 774 | 118 | 0.89 | 2.68 | 20.74 |
| 8 | SWIFT | 1 | % V/V | M-LRU | | | | | | | |
| 8 | COMPOUND 5 | 600 | MG/HA | LRU-BE | | | | | | | |
| 8 | SWIFT | 1 | % V/V | LRU-BE | | | | | | | |

The invention claimed is:

1. A method for effecting one or more of: reduction in the height of a *Papaver somniferum* plant, reduction in the lodging of a *Papaver somniferum* plant, reduction in the seed weight of a *Papaver somniferum* plant and increase in capsule weight of a *Papaver somniferum* plant, comprising the steps of applying an effective amount of a sulfonylurea compound or agriculturally acceptable salt or ester thereof to said *Papaver somniferum* plant or locus thereof.

2. A method according to claim 1 for reducing the height of a *Papaver somniferum* plant comprising the step of applying a height reducing effective amount of a sulfonylurea compound or agriculturally acceptable salt or ester thereof to said *Papaver somniferum* plant or locus thereof.

3. A method according to claim 1 for reducing lodging of a *Papaver somniferum* plant comprising the step of applying a lodging reducing effective amount of a sulfonylurea compound or agriculturally acceptable salt or ester thereof to said *Papaver somniferum* plant or locus thereof.

4. A method according to claim 1 for reducing the seed weight of a *Papaver somniferum* plant comprising the step of applying a seed weight reducing effective amount of a sulfonylurea compound or agriculturally acceptable salt or ester thereof to said *Papaver somniferum* plant or locus thereof.

5. A method according to claim 1 for increasing the capsule weight of a *Papaver somniferum* plant comprising the step of applying a capsule weight increasing effective amount of a sulfonylurea compound or agriculturally acceptable salt or ester thereof to said *Papaver somniferum* plant or locus thereof.

6. A method of increasing straw weight obtained from a *Papaver somniferum* plant comprising the step of applying a straw weight increasing effective amount of a sulfonylurea compound or agriculturally acceptable salt or ester thereof to said *Papaver somniferum* plant or locus thereof.

7. A method of increasing alkaloid yield and/or recovery from a *Papaver somniferum* plant comprising the step of applying an alkaloid yield and/or recovery increasing effective amount of a sulfonylurea compound or agriculturally acceptable salt or ester thereof to said *Papaver somniferum* plant or locus thereof.

8. A method according to claim 1 wherein the sulfonylurea compound is a compound of formula (1):

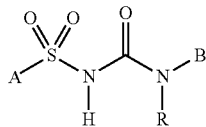

(1)

wherein A and B are independently an optionally substituted aryl or optionally substituted heteroaryl group, and R is H or $C_{1-4}$ alkyl.

9. A method according to claim 8 wherein the sulfonylurea compound is a compound of formula (1 a):

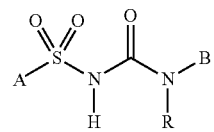

(1a)

wherein A is an optionally substituted phenyl group or a 5-6-membered or 9-10-membered heteroaryl group; and B is optionally substituted 5-6-membered heteroaryl group.

10. A method according to claim 9 wherein B is an optionally substituted triazinyl or pyrimidinyl group.

11. A method according to claim 9 wherein A is an optionally substituted phenyl, pyridinyl, pyrimidinyl, thienyl, imidazo-pyridinyl or pyrazolyl group.

12. A method according to claim 9 wherein the sulfonylurea compound is selected from the group consisting of amidosulfuron, azimsulfuron, benzulfuron, chlorimuron, cyclosulfamuron, ethoxysulfuron, flazasulfuron, flucetasulfuron, halosulfuron, imazosulfuron, mesosulfuron, nicosulfuran, orthosulfamuron, oxasulfuron, primisulfuron, pyrazosulfuron, rimsulfuron, sulfometuron, sulfosulfuron, trifloxysulfuron, chlorosulfuron, ethametsulfuron, iodosulfuron, metasulfuron, prosulfuron, thifensulfuron, triasulfuron, tribenuron, triflusulfuron and tritosulfuron and their agriculturally acceptable salts and esters thereof.

13. A method according to claim 12 wherein the sulfonylurea compound is selected from metasulfuron methyl, triasulfuron, mesosulfuron-methyl, thifensulfuron methyl and sulfosulfuron.

14. A method according to claim 1 wherein the sulfonylurea compound is applied at a rate of less than 1g a.i per hectare.

15. A method according to claim 14 wherein the sulfonylurea compound is applied at a rate of from 5 to 800mg a.i per hectare.

16. A method according to claim 1 wherein the sulfonylurea compound is applied at one or more stages of: 4-6 leaf, 6-8 leaf, 8-10 leaf, row cover, ground cover, early run-up, mid run-up, late run-up, bud emergence, bud to hook, hook and flowering.

17. A method of obtaining alkaloid from a *Papaver somniferum* plant comprising the steps of:
(i) applying an amount of a sulfonylurea compound or agriculturally acceptable salt or ester thereof which is effective in reducing the height, lodging or seed weight or increasing capsule weight, alkaloid yield or alkaloid recovery, to said *Papaver somniferum* plant or locus thereof;

(ii) harvesting *Papaver somniferum* capsules and forming a straw therefrom; and (iii) extracting the alkaloid from the straw.

18. A method of obtaining alkaloid from a *Papaver somniferum* plant comprising the steps of:

(i) applying an amount of a sulfonylurea compound or agriculturally acceptable salt or ester thereof which is effective in reducing the height, lodging or seed weight or increasing capsule weight, alkaloid yield or alkaloid recovery, to said *Papaver somniferum* plant or locus thereof;

(ii) harvesting opium from immature capsules; and (iii) extracting the alkaloid from the opium.

* * * * *